United States Patent
Gross et al.

(10) Patent No.: US 7,368,477 B2
(45) Date of Patent: May 6, 2008

(54) BENZOFURANYL ALKANAMINE DERIVATIVES AND USES THEREOF

(75) Inventors: Jonathan Laird Gross, Cranbury, NJ (US); Gary Paul Stack, Ambler, PA (US); Dahui Zhou, East Brunswick, NJ (US); Hong Gao, Belle Mead, NJ (US)

(73) Assignee: Wyeth, Madison, NJ (US)

( * ) Notice: Subject to any disclaimer, the term of this patent is extended or adjusted under 35 U.S.C. 154(b) by 99 days.

(21) Appl. No.: 11/408,319

(22) Filed: Apr. 21, 2006

(65) Prior Publication Data

US 2006/0247276 A1    Nov. 2, 2006

Related U.S. Application Data

(60) Provisional application No. 60/674,129, filed on Apr. 22, 2005.

(51) Int. Cl.
*A61K 31/4433* (2006.01)
*A61K 31/343* (2006.01)
*A61K 31/381* (2006.01)
*C07D 307/81* (2006.01)
*C07D 401/04* (2006.01)

(52) U.S. Cl. ............... 514/469; 514/337; 514/444; 546/284.1; 549/60; 549/467

(58) Field of Classification Search ............ 546/284.1; 549/60, 467; 514/337, 444, 469
See application file for complete search history.

(56) References Cited

U.S. PATENT DOCUMENTS

| | | | |
|---|---|---|---|
| 2,554,736 | A | 11/1951 | Haefliger et al. |
| 3,912,743 | A | 10/1975 | Christensen et al. |
| 4,007,196 | A | 2/1977 | Christensen et al. |
| 4,085,225 | A | 4/1978 | Welle et al. |
| 4,136,193 | A | 1/1979 | Bogeso et al. |
| 4,210,754 | A | 7/1980 | Burkard et al. |
| 4,229,449 | A | 10/1980 | Melloni et al. |
| 4,314,081 | A | 2/1982 | Molloy et al. |
| 4,478,836 | A | 10/1984 | Mouzin et al. |
| 4,535,186 | A | 8/1985 | Husbands et al. |
| 4,536,518 | A | 8/1985 | Welch et al. |
| RE34,712 | E | 8/1994 | Boegesoe et al. |
| 5,384,330 | A | 1/1995 | Dieter et al. |
| 5,565,483 | A | 10/1996 | Hewawasam et al. |
| 5,668,145 | A | 9/1997 | Bright |
| 5,705,646 | A | 1/1998 | Bright et al. |
| 5,712,303 | A | 1/1998 | Faraci et al. |
| 5,916,923 | A | 6/1999 | Rudolph et al. |
| 6,090,803 | A | 7/2000 | Failli et al. |
| 6,096,735 | A | 8/2000 | Ogawa et al. |
| 6,096,736 | A | 8/2000 | Ogawa et al. |
| 6,194,407 | B1 | 2/2001 | Failli et al. |
| 6,218,397 | B1 | 4/2001 | Chen |
| 6,274,171 | B1 | 8/2001 | Sherman et al. |
| 6,403,120 | B1 | 6/2002 | Sherman et al. |
| 6,419,958 | B2 | 7/2002 | Sherman et al. |
| 6,444,708 | B2 | 9/2002 | Rudolph et al. |
| 6,765,008 | B1 | 7/2004 | Chen |
| 6,967,201 | B1 | 11/2005 | Briner et al. |
| 7,045,545 | B1 | 5/2006 | Briner et al. |
| 2002/0183395 | A1 | 12/2002 | Argentieri et al. |
| 2004/0029949 | A1 | 2/2004 | Argentieri et al. |
| 2004/0235856 | A1 | 11/2004 | McMurray et al. |
| 2005/0124692 | A1 | 6/2005 | Gross et al. |
| 2005/0143452 | A1 | 6/2005 | Gross et al. |
| 2005/0261347 | A1 | 11/2005 | Gross et al. |
| 2006/0089405 | A1 | 4/2006 | Zhou |
| 2006/0111438 | A1 | 5/2006 | Gontcharov et al. |
| 2006/0241172 | A1 | 10/2006 | Zhou et al. |
| 2006/0241176 | A1 | 10/2006 | Stack et al. |
| 2006/0246551 | A1 | 11/2006 | Stack et al. |
| 2006/0247276 | A1 | 11/2006 | Gross et al. |
| 2006/0252825 | A1 | 11/2006 | Tadayon et al. |
| 2006/0258639 | A1 | 11/2006 | Logue et al. |
| 2006/0258711 | A1 | 11/2006 | Rosenzweig-Lipson |
| 2006/0258712 | A1 | 11/2006 | Jacobson |
| 2006/0258713 | A1 | 11/2006 | Rosenzweig-Lipson |
| 2006/0258714 | A1 | 11/2006 | Heffernan et al. |
| 2006/0258715 | A1 | 11/2006 | Jandura et al. |
| 2006/0258739 | A1 | 11/2006 | Ai et al. |

FOREIGN PATENT DOCUMENTS

WO    WO 2006/000902    5/2006

OTHER PUBLICATIONS

U.S. Appl. No. 11/787,929, Yu, et al.

(Continued)

*Primary Examiner*—Patricia L. Morris
(74) *Attorney, Agent, or Firm*—Julie Anne Knight; Andrea L. C. Robidoux; Choate Hall & Stewart LLP

(57) ABSTRACT

Compounds of formula I or pharmaceutically acceptable salts thereof are provided:

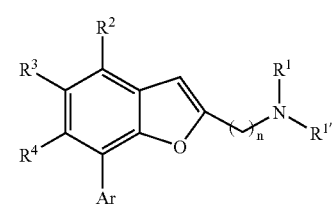

wherein each of $R^1$, $R^{1'}$, $R^2$, $R^3$, $R^4$, n, and Ar are as defined, and described in classes and subclasses herein, which are agonists or partial agonists of the 2C subtype of brain serotonin receptors. The compounds, and compositions containing the compounds, can be used to treat a variety of central nervous system disorders such as schizophrenia.

16 Claims, No Drawings

OTHER PUBLICATIONS

U.S. Appl. No. 11/787,860, Gontcharov et al.
U.S. Appl. No. 11/726,941, Rosenzweig-Lipson.
U.S. Appl. No. 11/787,663, Mirmehrabi.
Allison, et al., *Am. J. Psychiatry*, 156: 1686-96, 1999.
Battegay, et al., *Neuropsychobiology*, 13:31, 1985.
Benefield, et al., *Drugs*, 32: 313, 1986.
Bishop, et al., *Expert Opin. Ther. Patent*, 13: 1691-1705, 2003.
Bundgaard (ed), *Design of Prodrugs*, Elsevier, Ch. 1(p. 1-92), Ch.4(p. 157-176), Ch.5(p. 177-198), and Ch.6(199-241), 1985.
Bundgaard, et al., *Journal of Drug Delivery Reviews*, 8: 1-38, 1992.
Bundgaard, *J. of Pharmaceutical Sciences*, 77: 285-298, 1988.
Christensen, et al., *Eur. J. Pharmacol.*, 41: 153, 1977.
Claassen, et al, *Brit. J. Pharmacol.*, 60: 505, 1977.
Cowen, et al., *Human Psychopharmacology*, 10: 385-91, 1995.
De Wilde, et al., *Affective Disord.*, 4: 249, 1982.
Di Giovanni, et al., *Synapse*, 35: 53-61, 2000.
Di Matteo, et al., *Neuropharmacology*, 37: 265-272, 1998.
Di Matteo, et al., *Neuropharmacology*, 38: 1195-1205, 1999.
Dufour, et al., *Int. Clin. Psychopharmacol.*, 2: 225, 1987.
Fox, et al., *Experimental Neurology*, 151: 35-49, 1998.
Hassan, et al., *Brit J. Clin. Pharmacol*, 19: 705, 1985.
Lassen, *Eur. J. Pharmacol*, 47: 351, 1978.
Laursen, et al., *Acta Psychiat. Scand.* 71: 249, 1985.
Lowry, et al., *J. Biol. Chem.*, 193: 265, 1951.
Masand, "Weight gain associated with psychotropic drugs", *Exp. Opin. Pharmacother*. I: 377-89, 2000.
Mendell, et al., *N. Engl. J. Med.*, 348: 1243-55, 2003.
Millan, et al., *Neuropharmacology*, 37: 953-55, 1998.
Moret, et al., *Neuropharamacology*, 24: 1211-19, 1985.
Robertson, et al., *J. Med. Chem.*, 31: 1412, 1988.
Rosenzwieg-Lipson, et al., "Antiobesity-like effects of the selective 5-HT2C agonist way", *ASPET abstract*, 2000.
Whitaker, *Spectrum Life Sciences Decision Resources*, 2: 1-9, 2000.
Widder, et al (ed.), Methods in Enzymolgoy, *Academic Press*, 112:56-67, 1985.

BENZOFURANYL ALKANAMINE DERIVATIVES AND USES THEREOF

CROSS REFERENCE TO RELATED APPLICATIONS

This application claims priority to U.S. Provisional Patent Application Ser. No. 60/674,129, filed Apr. 22, 2005, the entirety of which is hereby incorporated herein by reference.

FIELD OF THE INVENTION

The present invention relates to 5-$HT_{2C}$ receptor agonists, processes for their preparation, and uses thereof.

BACKGROUND OF THE INVENTION

Schizophrenia affects approximately 5 million people. The most prevalent treatments for schizophrenia are currently the 'atypical' antipsychotics, which combine dopamine ($D_2$) and serotonin (5-$HT_{2A}$) receptor antagonism. Despite the reported improvements in efficacy and side-effect liability of atypical antipsychotics relative to typical antipsychotics, these compounds do not appear to adequately treat all the symptoms of schizophrenia and are accompanied by problematic side effects, such as weight gain (Allison, D. B., et. al., Am. J. Psychiatry, 156: 1686-1696, 1999; Masand, P. S., Exp. Opin. Pharmacother. I: 377-389, 2000; Whitaker, R., Spectrum Life Sciences. Decision Resources. 2:1-9, 2000).

Atypical antipsychotics also bind with high affinity to 5-$HT_{2C}$ receptors and function as 5-$HT_{2C}$ receptor antagonists or inverse agonists. Weight gain is a problematic side effect associated with atypical antipsychotics such as clozapine and olanzapine, and it has been suggested that 5-$HT_{2C}$ antagonism is responsible for the increased weight gain. Conversely, stimulation of the 5-$HT_{2C}$ receptor is known to result in decreased food intake and body weight (Walsh et. al., Psychopharmacology 124: 57-73, 1996; Cowen, P. J., et. al., Human Psychopharmacology 10: 385-391, 1995; Rosenzweig-Lipson, S., et. al., ASPET abstract, 2000).

Several lines of evidence support a role for 5-$HT_{2C}$ receptor agonism or partial agonism as a treatment for schizophrenia. Studies suggest that 5-$HT_{2C}$ antagonists increase synaptic levels of dopamine and may be effective in animal models of Parkinson's disease (Di Matteo, V., et. al., Neuropharmacology 37: 265-272, 1998; Fox, S. H., et. al., Experimental Neurology 151: 35-49, 1998). Since the positive symptoms of schizophrenia are associated with increased levels of dopamine, compounds with actions opposite to those of 5-$HT_{2C}$ antagonists, such as 5-$HT_{2C}$ agonists and partial agonists, should reduce levels of synaptic dopamine. Recent studies have demonstrated that 5-$HT_{2C}$ agonists decrease levels of dopamine in the prefrontal cortex and nucleus accumbens (Millan, M. J., et. al., Neuropharmacology 37: 953-955, 1998; Di Matteo, V., et. al., Neuropharmacology 38: 1195-1205, 1999; Di Giovanni, G., et. al., Synapse 35: 53-61, 2000), brain regions that are thought to mediate critical antipsychotic effects of drugs like clozapine. However, 5-$HT_{2C}$ agonists do not decrease dopamine levels in the striatum, the brain region most closely associated with extrapyramidal side effects. In addition, a recent study demonstrates that 5-$HT_{2C}$ agonists decrease firing in the ventral tegmental area (VTA), but not in the substantia nigra. The differential effects of 5-$HT_{2C}$ agonists in the mesolimbic pathway relative to the nigrostriatal pathway suggest that 5-$HT_{2C}$ agonists have limbic selectivity, and will be less likely to produce extrapyramidal side effects associated with typical antipsychotics.

SUMMARY OF THE INVENTION

The present invention relates to 5-$HT_{2C}$ agonists and uses thereof. In one aspect, the invention relates to novel 7-aryl-(1-benzofuran-2-yl)alkanamine derivatives that act as agonists or partial agonists of the 5-$HT_{2C}$ receptor. The compounds are useful, for example, to treat schizophrenia and the concomitant mood disorders and cognitive impairments of schizophrenia. In certain embodiments, compounds of the present invention are less likely to produce the body weight increases associated with current atypical antipsychotics. The compounds of the present invention are also useful for the treatment of obesity and its comorbidities.

In certain embodiments, the present invention provides a compound of formula I:

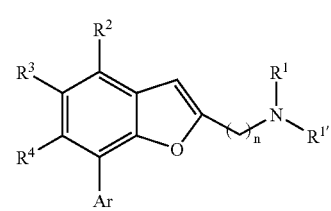

I or pharmaceutically acceptable salts thereof, wherein:

each of $R^1$ and $R^{1'}$ is independently hydrogen, methyl, ethyl, 2-fluoroethyl, 2,2-difluoroethyl or cyclopropyl;

each of $R^2$, $R^3$ and $R^4$ is independently hydrogen, halogen, OH, lower alkyl, lower alkoxy, trifluoromethyl, trifluoromethoxy, or CN;

Ar is thienyl, furyl, pyridyl, or phenyl wherein Ar is optionally substituted with one or more $R^x$ groups;

each $R^x$ is independently halogen, —OH, —CN, lower alkyl, lower alkoxy, —$CF_3$, or —$OCF_3$; and n is one or two.

In certain other embodiments, the invention relates to methods for treating a patient suffering from schizophrenia, schizophreniform disorder, schizoaffective disorder, delusional disorder, substance-induced psychotic disorder, L-DOPA-induced psychosis, psychosis associated with Alzheimer's dementia, psychosis associated with Parkinson's disease, psychosis associated with Lewy body disease, dementia, memory deficit, intellectual deficit associated with Alzheimer's disease, bipolar disorders, depressive disorders, mood episodes, anxiety disorders, adjustment disorders, eating disorders, epilepsy, sleep disorders, migraines, sexual dysfunction, substance abuse, addiction to alcohol and various other drugs, including cocaine and nicotine, gastrointestinal disorders, obesity, or a central nervous system deficiency associated with trauma, stroke, or spinal cord injury that includes administering to the patient a therapeutically effective amount of a compound of formula I, or a pharmaceutically acceptable salt thereof.

In still other embodiments, the invention relates to compositions comprising a compound of formula I or a pharmaceutically acceptable salt thereof, and one or more pharmaceutically acceptable carriers, excipients, or diluents.

DETAILED DESCRIPTION OF THE INVENTION

1. Compounds and Definitions:

The present invention relates to novel 7-[aryl]-(1-benzofuran-2-yl)alkanamine derivatives that are agonists or partial agonists of the 2C subtype of brain serotonin receptors.

The term "lower alkyl," as used herein, refers to a hydrocarbon chain having up to 4 carbon atoms, preferably 1 to 3 carbon atoms, and more preferably 1 to 2 carbon atoms. The term "alkyl" includes, but is not limited to, straight and branched chains such as methyl, ethyl, n-propyl, isopropyl, n-butyl, isobutyl, sec-butyl, or t-butyl.

The term "alkoxy," as used herein, refers to the group —OR*, wherein R* is a lower alkyl group.

The terms "halogen" or "halo," as used herein, refer to chlorine, bromine, fluorine or iodine.

The terms "effective amount" and "therapeutically effective amount," as used herein, refer to the amount of a compound of formula I that, when administered to a patient, is effective to at least partially treat a condition from which the patient is suffering from. Such conditions include, but are not limited to, schizophrenia, schizoaffective disorder, schizophreniform disorder, L-DOPA-induced psychosis, bipolar disorder, obesity, obsessive compulsive disorder, depression, panic disorder, sleep disorders, eating disorders, and epilepsy.

The term "pharmaceutically acceptable salts" or "pharmaceutically acceptable salt" includes acid addition salts, namely salts derived from treating a compound of formula I with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, or similarly known acceptable acids. In certain embodiments, the present invention provides the hydrochloride salt of a compound of formula I. Where the compound having formula I has an acidic function, for instance, where $R^2$, $R^3$ or $R^4$ is phenolic hydroxyl, the term "pharmaceutically acceptable salts" or "pharmaceutically acceptable salt" includes salts derived from bases, for instance sodium salts.

The term "patient," as used herein, refers to a mammal. In certain embodiments, the term "patient", as used herein, refers to a human.

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The terms "treat" or "treating," as used herein, refers to partially or completely alleviating, inhibiting, preventing, ameliorating and/or relieving the condition.

The terms "suffer" or "suffering" as used herein refers to one or more conditions that a patient has been diagnosed with, or is suspected to have.

2. Description of Exemplary Compounds:

In certain embodiments, the invention relates to a compound of formula I:

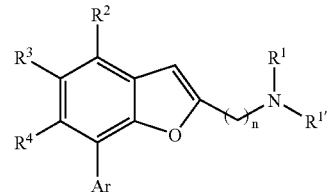

or pharmaceutically acceptable salts thereof, wherein:

each of $R^1$ and $R^{1'}$ is independently hydrogen, methyl, ethyl, 2-fluoroethyl, 2,2-difluoroethyl or cyclopropyl;

each of $R^2$, $R^3$ and $R^4$ is independently hydrogen, halogen, OH, lower alkyl, lower alkoxy, trifluoromethyl, trifluoromethoxy, or CN;

Ar is thienyl, furyl, pyridyl, or phenyl wherein Ar is optionally substituted with one or more $R^x$ groups;

each $R^x$ is independently halogen, —OH, —CN, lower alkyl, lower alkoxy, —$CF_3$, or —$OCF_3$; and n is one or two.

In certain embodiments, the n group of formula I is 1.

In other embodiments, the n group of formula I is 2.

As defined generally above, each of the $R^1$ and $R^{1'}$ groups of formula I is independently hydrogen, methyl, ethyl, 2-fluoroethyl, 2,2-difluoroethyl or cyclopropyl. In certain embodiments, one of the $R^1$ and $R^{1'}$ groups of formula I is hydrogen and the other of $R^1$ and $R^{1'}$ groups of formula I is hydrogen, methyl, ethyl, 2-fluoroethyl, 2,2-difluoroethyl or cyclopropyl. In other embodiments, neither of the $R^1$ and $R^{1'}$ groups of formula I is hydrogen. In still other embodiments, both of the $R^1$ and $R^{1'}$ groups of formula I are hydrogen.

As defined generally above, each of the $R^2$, $R^3$ and $R^4$ groups of formula I is independently hydrogen, halogen, OH, lower alkyl, lower alkoxy, trifluoromethyl, trifluoromethoxy, or CN. In certain embodiments, the $R^2$, $R^3$ and $R^4$ groups of formula I are all hydrogen. In other embodiments, at least one of the $R^2$, $R^3$ and $R^4$ groups of formula I is halogen. According to another aspect of the present invention, the $R^2$ group of formula I is hydrogen and the $R^3$ and $R^4$ groups of formula I are independently halogen, OH, lower alkyl, lower alkoxy, trifluoromethyl, trifluoromethoxy, or CN. Yet another aspect of the present invention provides a compound of formula I wherein $R^2$ and $R^4$ are both hydrogen and $R^3$ is lower alkyl or lower alkoxy. Yet another aspect of the present invention provides a compound of formula I wherein $R^2$ and $R^4$ are both hydrogen and $R^3$ is halogen. In certain embodiments, the $R^2$ and $R^4$ groups of formula I are both hydrogen and $R^3$ is fluoro or chloro. In other embodiments, the $R^2$ and $R^3$ groups of formula I are both hydrogen and $R^4$ is fluoro or chloro.

As defined generally above, the Ar group of formula I is thienyl, furyl, pyridyl, or phenyl, wherein Ar is optionally substituted with one or more $R^x$ subsituents, wherein each $R^x$ is independently selected from halogen, —OH, —CN, lower alkyl, lower alkoxy, —$CF_3$, or —$OCF_3$. In certain embodiments, the Ar group of formula I is unsubstituted phenyl. In other embodiments, the Ar group of formula I is phenyl with at least one substituent in the ortho position. In other embodiments, the Ar group of formula I is phenyl with at least one substituent in the ortho position selected from halogen, lower alkyl, lower alkoxy, or trifluoromethyl. According to one aspect the present invention provides a compound of formula I wherein Ar is phenyl di-substituted in the ortho and meta positions with halogen, lower alkyl, or lower alkoxy. Yet another aspect of the present invention provides a compound of formula I wherein Ar is phenyl di-subsituted in the ortho and para positions with halogen, lower alkyl, or lower alkoxy. Yet another aspect of the present invention provides a compound of formula I wherein Ar is phenyl di-subsituted in both ortho positions with halogen, lower alkyl, or lower alkoxy. Exemplary substituents on the phenyl moiety of the Ar group of formula I include OMe, fluoro, chloro, methyl, and trifluoromethyl.

In certain embodiments, the Ar group of formula I is selected from the following:

i

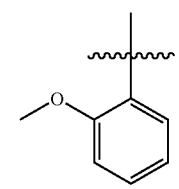

ii

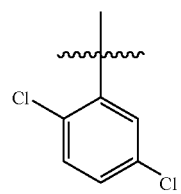

iii

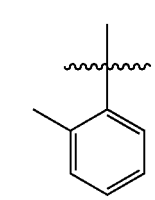

iv

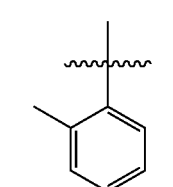

v

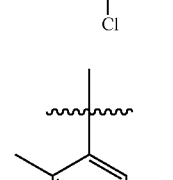

vi

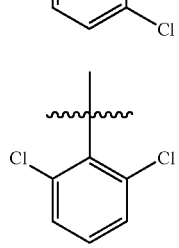

vii

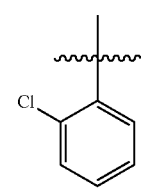

viii

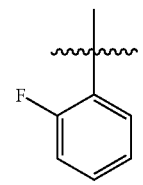

ix

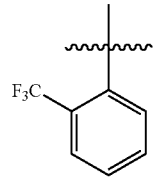

x

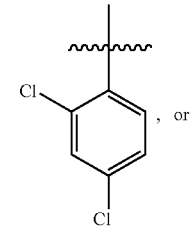, or xi

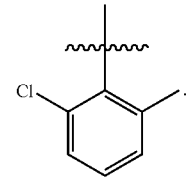.

According to another embodiment, the present invention provides a compound of formula II:

II

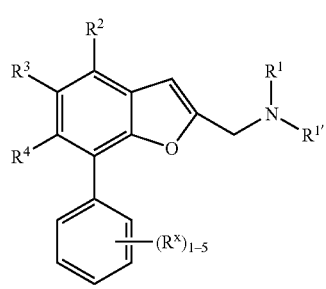

or pharmaceutically acceptable salts thereof, wherein each $R^x$ is independently halogen, OH, lower alkyl, lower alkoxy, trifluoromethyl, trifluoromethoxy, or CN, and each of $R^1$, $R^{1'}$, $R^2$, $R^3$ and $R^4$ are as defined generally above and in classes and subclasses described above and herein.

According to yet another embodiment, the present invention provides a compound of formula III:

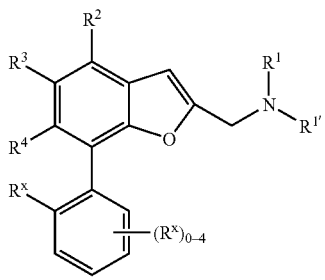

III or pharmaceutically acceptable salts thereof, wherein each $R^x$ is independently halogen, OH, lower alkyl, lower alkoxy, trifluoromethyl, trifluoromethoxy, or CN, and each of $R^1$, $R^{1'}$, $R^2$, $R^3$ and $R^4$ are as defined generally above and in classes and subclasses described above and herein.

According to yet another embodiment, the present invention provides a compound of formula IV:

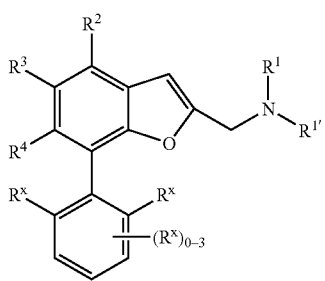

IV or pharmaceutically acceptable salts thereof, wherein each $R^x$ is independently halogen, OH, lower alkyl, lower alkoxy, trifluoromethyl, trifluoromethoxy, or CN, and each of $R^1$, $R^{1'}$, $R^2$, $R^3$ and $R^4$ are as defined generally above and in classes and subclasses described above and herein.

According to yet another embodiment, the present invention provides a compound of formula V:

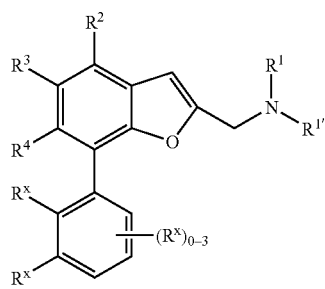

V or pharmaceutically acceptable salts thereof, wherein each $R^x$ is independently halogen, OH, lower alkyl, lower alkoxy, trifluoromethyl, trifluoromethoxy, or CN, and each of $R^1$, $R^{1'}$, $R^2$, $R^3$ and $R^4$ are as defined generally above and in classes and subclasses described above and herein.

According to yet another embodiment, the present invention provides a compound of formula VI:

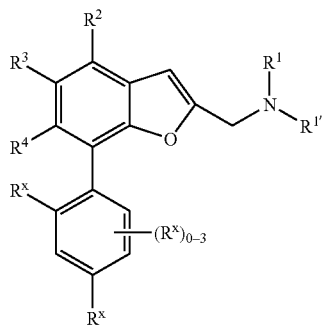

VI or pharmaceutically acceptable salts thereof, wherein each $R^x$ is independently halogen, OH, lower alkyl, lower alkoxy, trifluoromethyl, trifluoromethoxy, or CN, and each of $R^1$, $R^{1'}$, $R^2$, $R^3$ and $R^4$ are as defined generally above and in classes and subclasses described above and herein.

According to yet another embodiment, the present invention provides a compound of formula VII:

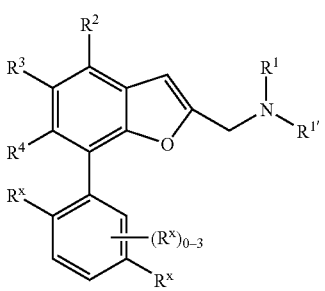

VII or pharmaceutically acceptable salts thereof, wherein each $R^x$ is independently halogen, OH, lower alkyl, lower alkoxy, trifluoromethyl, trifluoromethoxy, or CN, and each of $R^1$, $R^{1'}$, $R^2$, $R^3$ and $R^4$ are as defined generally above and in classes and subclasses described above and herein.

It is recognized that atropisomers of the present compounds may exit. The present invention thus encompasses atropisomeric forms of compounds of formula I as defined above, and in classes and sublcasses described above and herein.

Exemplary compounds of formula I are set forth in Table 1, below.

TABLE 1

Exemplary Compounds of Formula I:

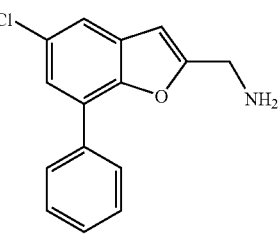

I-1

TABLE 1-continued
Exemplary Compounds of Formula I:
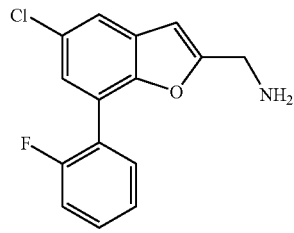
I-2
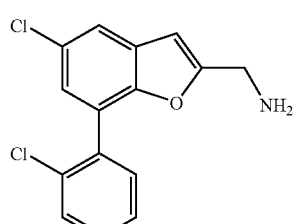
I-3
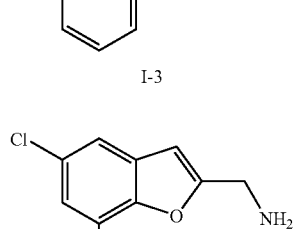
I-4
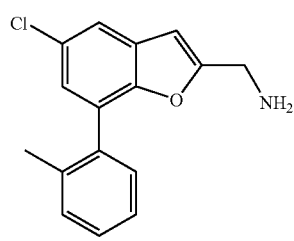
I-5
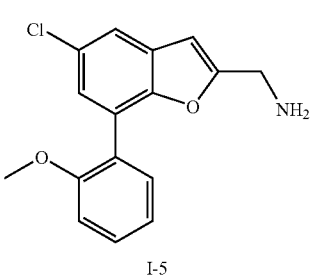
I-6
TABLE 1-continued
Exemplary Compounds of Formula I:
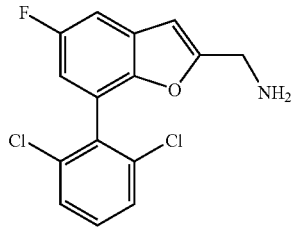
I-7
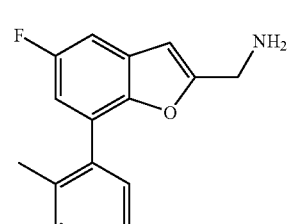
I-8
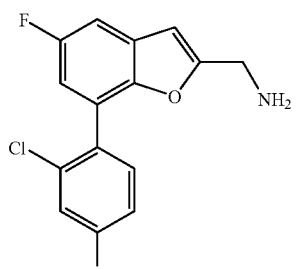
I-9
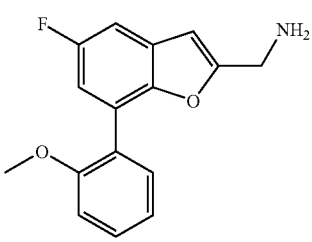
I-10
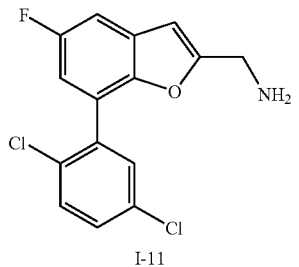
I-11

TABLE 1-continued

Exemplary Compounds of Formula I:

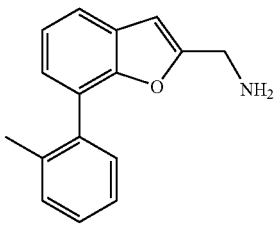

I-12

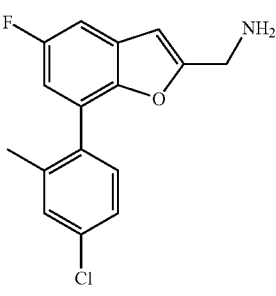

I-13

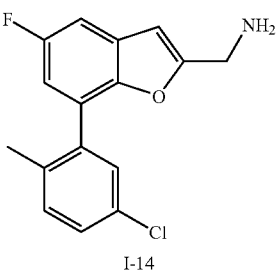

I-14

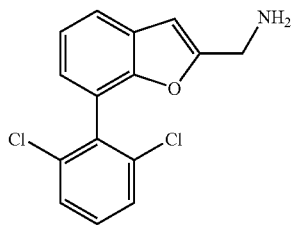

I-15

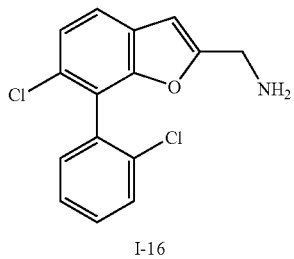

I-16

TABLE 1-continued

Exemplary Compounds of Formula I:

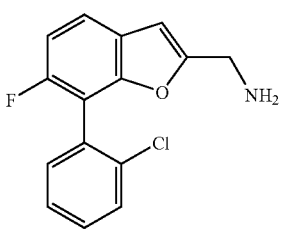

I-17

3. General Methods of Providing the Present Compounds:

The 7-[biaryl]-1-benzofuran-2-yl}methyl)amines of formula I may be prepared as illustrated by the following schemes. An appropriately substituted 2-bromo-6-hydroxybenzaldehyde or bromosalicylaldehyde (2) is reacted with diethyl bromomalonate in the presence of a suitable base such as potassium tert-butoxide in a solvent such tetrahydrofuran and ethanol (Scheme 1) to provide 2-carboalkoxybenzofuran (3). Additionally, the 2-carboalkoxybenzofuran (3) may be prepared via cyclization of the appropriately substituted bromosalicylaldehyde with ethyl bromacetate in the presence of a base such as potassium carbonate in a solvent such as N,N-dimethylformamide. The 2-bromo-6-hydroxybenzaldehydes appropriate for the synthesis of compounds of formula I are either known compounds or can be readily prepared by one skilled in the art. The resulting 2-carboalkoxybenzofuran (3) is then hydrolyzed with aqueous sodium hydroxide or other suitable alkoxide to provide a carboxylic acid that can then be reduced to the alcohol (4) by treatment with an appropriate reducing agent such as borane in tetrahydrofuran in a solvent such as tetrahydrofuran. Treatment of the alcohol (4) with phthalimide under standard Mitsunobu conditions, such as triphenylphoshine and diisopropylazodicarboxylate in a solvent such as toluene, provides the phthalimide (5). Introduction of the biaryl functionality is achieved by a palladium-catalyzed cross-coupling reaction (i.e. Suzuki reaction) with the desired boronic acid. Treatment of (5) with a catalyst such as dichlorobis(tri-o-tolylphosphine)-palladium(II) in the presence of a suitable base such as potassium carbonate in a solvent such as dioxane provides the biaryl product (5a). Subsequent removal of the phthalimide system by treatment of (5a) with methylamine in a solvent such as ethanol provides the compounds of formula I. Treatment of the phthalimide derivative 5a with methylamine in ethanol allows the mild deprotection of the terminal amino group to give the primary amine, namely a compound having formula I where each of $R^1$ and $R^{1'}$ is hydrogen. The primary amine may be converted into a secondary or tertiary amine conforming with formula I in known manner, for instance, by alkylation or reductive alkylation.

Scheme 1

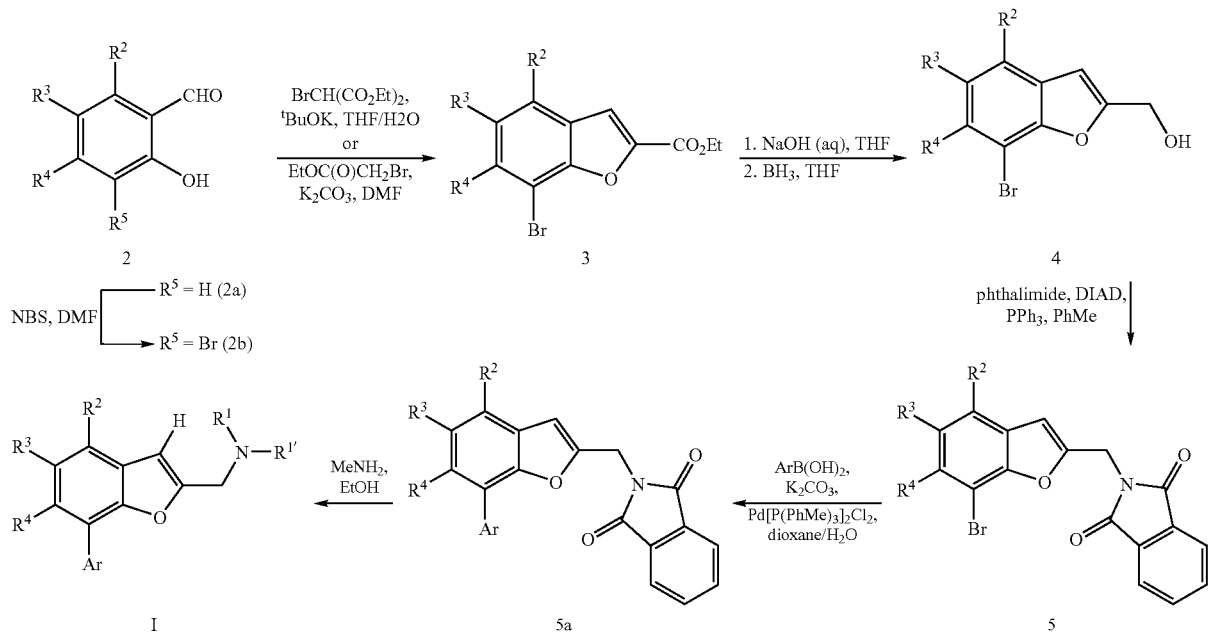

Alternatively, the biaryl system may be introduced directly onto the 2-carboalkoxybenzofuran (3) via a palladium-catalyzed cross-coupling reaction (i.e. Suzuki reaction). Treatment of the 2-carboalkoxy-7-methoxybenzofuran (3a) with boron tribromide (Scheme 1a) in a solvent such as dichloromethane provides the phenol (3b). Reaction of the phenol (3b) with trifluoromethanesulfonic anhydride in the presence of a base such as triethylamine in a solvent such as dichloromethane provides the triflate (3c). Introduction of the biaryl functionality is achieved by a palladium-catalyzed cross-coupling reaction (i.e. Suzuki reaction) with the desired boronic acid. Therefore, treatment of either (3) or (3a) with a catalyst such as dichlorobis(tri-o-tolylphosphine)-palladium(II) in the presence of a suitable base such as potassium carbonate in a solvent such as dioxane provides the biaryl product (3d). The carboalkoxy functionality present in (3d) can be reduced with a suitable reducing agent such as lithium borohydride in a solvent such as tetrahydrofuran to provide the alcohol (4a) directly. Reaction of the alcohol (4a) with phthalimide under standard Mitsunobu conditions, such as triphenylphoshine and diisopropylazodicarboxylate in a solvent such as toluene, provides the phthalimide (5a).

Scheme 1a

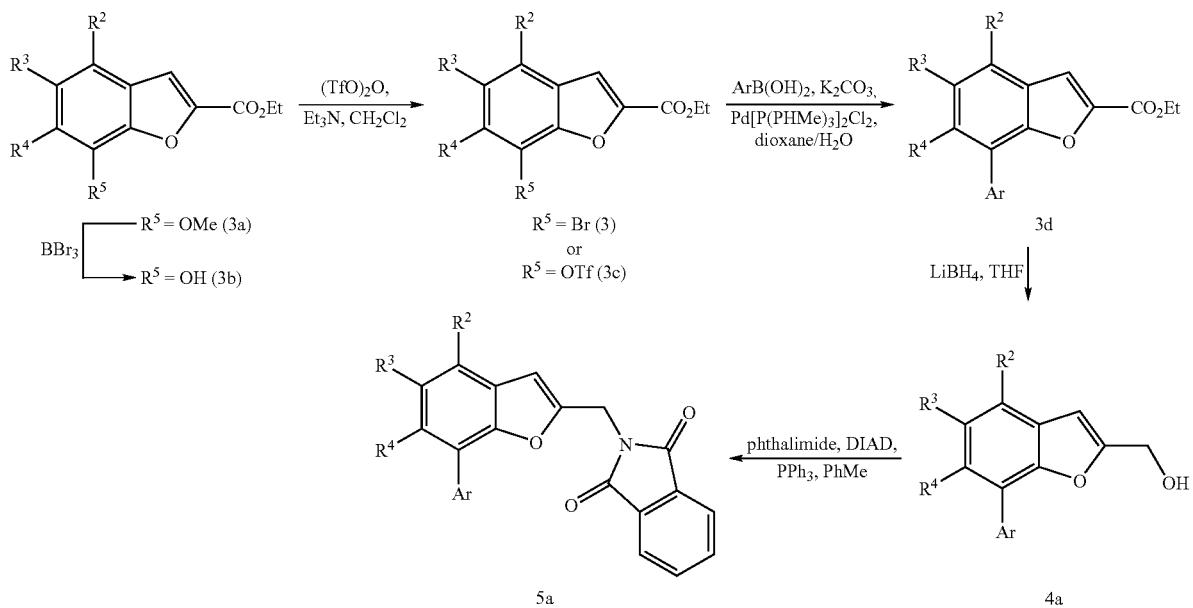

For certain compounds of formula I, it is useful to introduce the biaryl system at the beginning of the synthesis via a palladium-catalyzed cross-coupling reaction (i.e. Suzuki reaction) of an appropriately substituted 2-methoxy-bromobenzene (6) with the desired boronic acid (Scheme 2). Treatment of (6) with a catalyst such as tetrakis(triphenylphosphine)palladium(0) in the presence of a suitable base such as potassium carbonate in a solvent such as ethylene glycol dimethyl ether provides the biaryl methoxybenzene (6a). Removal of the methoxy group in (6a) is accomplished with hydrogen bromide (30 wt % in acetic acid) to provide phenol (6b). The phenol (6b) is alkylated with an appropriately substituted allyl bromide or alcohol in the presence of a suitable base such as potassium carbonate in a solvent such as N,N-dimethylformamide to afford the allyl ether (7). The resulting allyl ether (7) is treated in refluxing mesitylene or other suitable high boiling solvent to afford the desired Claisen rearrangement product (8). The double bond present in (8) is isomerized by refluxing with bis(acetonitrile)dichloropalladium(II) in a solvent such as dichloromethane to provide the 2-propenyl phenol (9). Oxidation of the double bond present in (9) by treatment with osmium tetroxide and sodium periodate in a solvent system such as tetrahydrofuran and water provides the 2-hydroxybenzaldehyde (2c).

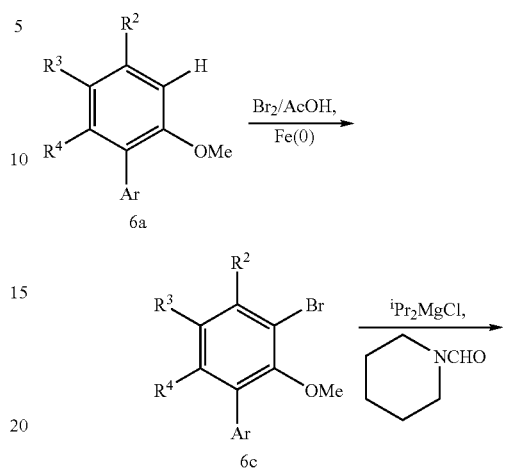

Scheme 2a

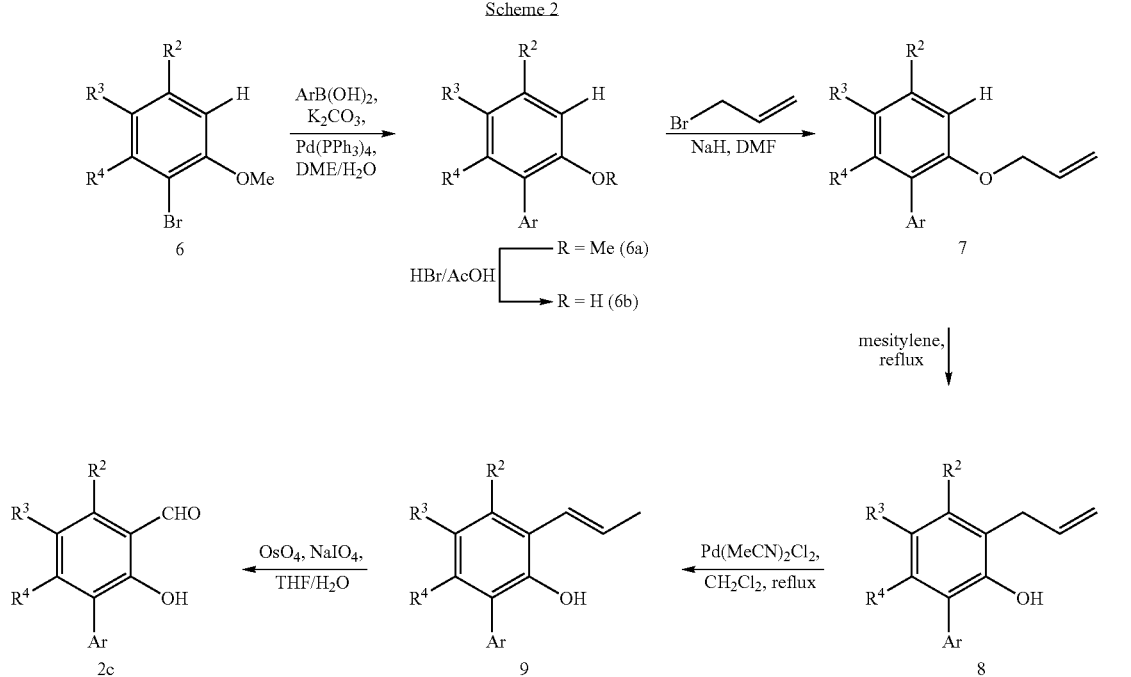

Scheme 2

Alternatively, treatment of the methoxybenzene (6a) with bromine in acetic acid in the presence of iron(0) provides the 2-bromomethoxybenzene (6c). Reaction of (6c) with isopropylmagnesium chloride and 1-formylpiperidine in a solvent such as tetrahydrofuran affords the 2-methoxybenzaldehyde (2d). Removal of the methyl group is accomplished by reaction of the 2-methoxybenzaldehyde (2d) with boron tribromide in a solvent such as dichloromethane to give the 2-hydroxybenzaldehyde (2c).

-continued

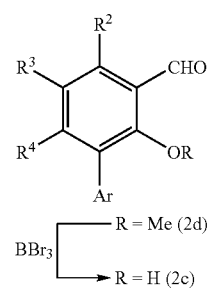

Alternatively, treatment of the biaryl phenol (6b) with 1,1-dichlorodimethyl ether in the presence of titanium tetrachloride in a solvent such as dichloromethane provides the 2-hydroxybenzaldehyde (2c) directly.

Scheme 2b

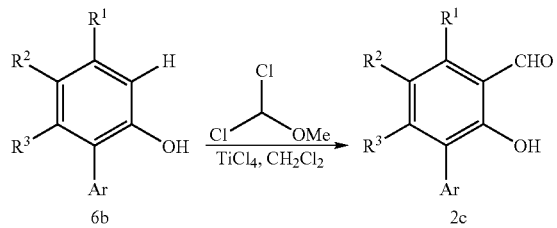

Although certain exemplary embodiments are depicted and described above and herein, it will be appreciated that compounds of the invention can be prepared according to the methods described generally above using appropriate starting materials by methods generally available to one of ordinary skill in the art. Additional embodiments are exemplified in more detail herein.

4. Uses, Formulation and Administration

Compounds of the present invention have affinity for and agonist or partial agonist activity at the 2C subtype of brain serotonin receptors and are thus of interest for the treatment of a variety of disorders and/or the alleviation of one or more associated symptoms. Such disorders associated with modulations of the 2C subtype of brain serotonin receptors are described in detail below. The present invention contemplates that compounds of the present invention are associated with a rapid onset of action. In addition, compounds of the present invention lack the side-effect of sexual dysfunction.

Compounds of the present invention are useful for treating one or more psychotic disorders, as described herein, without causing diabetogenesis. Diabetogenesis is a side-effect associated with atypical antipsychotic agents. Without wishing to be bound by any particular theory, it is believed that the diabetogenesis associated with atypical antipsychotic agents results from the fact that those agents are 5-HT$_{2C}$ antagonists. As described herein, the present compounds are 5-HT$_{2C}$ agonists, or partial agonists, and therefore are not associated with diabetogenesis.

Compounds of the present invention are useful for treating one or more psychotic disorders such as schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; and psychosis associated with Lewy body disease.

Compounds of the present invention are also useful for treating symptoms related to psychotic disorders of the schizophrenic types, including the so called "positive" and "negative" symptoms of schizophrenia. These symptoms include for example hallucinations, delusions, paranoia, anxiety, agitation, excessive aggression, tension, thought disorder, blunted affect, and social or emotional withdrawal in psychotic patients. Other symptoms often associated with psychotic disorders include cognition disorders or deficits such as poor attention and impaired function, depression, suicide, metabolic syndrome, and substance abuse. Thus, another embodiment of the present invention provides a method for treating one or more symptoms associated with a psychotic disorder.

In other embodiments, the present compounds are useful for treating anxiety disorders such as panic attack, agoraphobia, panic disorder, specific phobia, social phobia, social anxiety disorder, obsessive compulsive disorder, posttraumatic stress disorder, acute stress disorder, generalized anxiety disorder, separation anxiety disorder, substance-induced anxiety disorder, and anxiety disorder not otherwise specified.

According to another embodiment, the present compounds are useful for treating bipolar disorders. Such bipolar disorders include bipolar I disorder, bipolar II disorder, and cyclothymic disorder; bipolar mania, dementia, and depression with psychotic features. The present compounds are also useful for treating (including the preventing) of cycling that may occur between bipolar depression and bipolar mania.

A more complete description of the aforementioned mental disorders can be found in the Diagnostic and Statistical Manual of Mental Disorders, 4$^{th}$ edition, Washington, D.C., American Psychiatric Association (1994), incorporated herein by reference in its entirety.

In certain embodiments, compounds of the present invention are administered in combination with one or more anti-psychotic agents. Such anti-psychotic agents are well known in the art and include clozapine (e.g., Clozaril®), risperidone (e.g., Risperidal®), olanzapine (e.g., Zyprexa®), quetiapine (e.g., Seroquel®), ziprasidone (e.g., Geodon®), aripiprazole, amisulpiride, chlorpromazine, fluphenazine, haloperidol (e.g., Haldol®), loxapine, mesoridazine, molindone, perphenazine, pimozide, seroquel, sulpiride, thioridazine, thiothixene, trifluoperazine, and bifeprunox to name a few.

The combination of a compound of the present invention with one or more anti-psychotic agents is useful for treating schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; psychosis associated with Lewy body disease; bipolar disorders such as bipolar I disorder, bipolar II disorder, and cyclothymic disorder; bipolar mania, dementia, and depression with psychotic features. In some embodiments, these combinations are useful in the treatment of bipolar disorder, including for example treating the cycling between bipolar depression and bipolar mania.

In other embodiments, administration of a compound of the present invention with an anti-psychotic agent provide anti-psychotic benefits while eliminating or minimizing certain side affects (e.g., akathisia, dystonia, Parkinsonism dyskinesia and late dyskinesia and the like) typically observed when the anti-psychotic agent(s) is/are taken alone.

In other embodiments, compounds of the present invention are useful for treating one or more depressive disorders such as major depressive disorder, seasonal affective disorder, dysthymic disorder, substance-induced mood disorder, depressive disorder not otherwise specified, and treatment resistant depression.

Another aspect of the present invention provides a method for treating one or more mood episodes such as major depressive episode, manic episode, mixed episode, and hypomanic episode; and adjustment disorders such as adjustment disorders with anxiety and/or depressed mood.

Compounds of the present invention are also useful for treating symptoms related to depressive disorders including somatic symptoms such as neuropathic pain and sexual dysfunction. Other somatic symptoms include hopelessness, helplessness, anxiety and worries, memory complaints with or without objective signs of cognitive impairment, loss of feeling of pleasure (anhedonia), slowed movement, irritability, and lack of interest in personal care, such as poor adherence to medical or dietary regimens.

In certain embodiments, the present invention provides a method of treating sexual dysfunction related to depression. In other embodiments, the present invention provides a method of treating sexual dysfunction associated with administering a serotonin reuptake inhibitor (SRI) for treating a depressive or other disorder. Such methods of treating sexual dysfunction are described in detail below.

In certain embodiments, compounds of the present invention are administered in combination with one or more antidepressive agents. Suitable antidepressant agents include, for example, serotonin reuptake inhibitors (SRIs), norepinephrine reuptake inhibitors (NRIs), combined serotonin-norepinephrine reuptake inhibitors (SNRIs), monoamine oxidase inhibitors (MAOIs), reversible inhibitors of monoamine oxidase (RIMAs), phosphodiesterase-4 (PDE4) inhibitors, corticotropin releasing factor (CRF) antagonists, alpha.-adrenoreceptor antagonists or other compounds including atypical antidepressants. Additional antidepressants for administering in combination with compounds of the present invention include triple uptake inhibitors such as DOV 216303 and DOV 21947 . . . ; melatonin agonists such as agomelotine, super neurotransmitter uptake blockers (SNUBs; e.g., NS-2389 from GlaxoSmithKline and Neurosearch; (R)-DDMA from Sepracor), and/or substance P/neurokinin receptor antagonists (e.g., aprepitant/MK-869 from Merck; NKP-608 from Novartis; CPI-122721 from Pfizer; R673 from Roche; TAK637 from Takeda; and GW-97599 from GlaxoSmithKline).

Another class of antidepressant agents for administering in combination with compounds of the present invention are noradrenergic and specific serotonergic antidepressants (NaSSAs). A suitable example of a NaSSA is mirtazepine.

Suitable NRIs for administering in combination with compounds of the present invention include tertiary amine tricyclics and secondary amine tricyclics. Suitable examples of tertiary amine tricyclics include: amitriptyline, clomipramine, doxepin, imipramine (See U.S. Pat. No. 2,554,736, incorporated herein by reference in its entirety) and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Another NRI for administering in combination with compounds of the present invention is reboxetine (Edronax™; 2-[.alpha.-(2-ethoxy)phenoxy-benzyl]morpholine, usually administered as the racemate; See U.S. Pat. No. 4,229,449, incorporated herein by reference in its entirety).

Suitable SSRIs for administering in combination with compounds of the present invention include: citalopram (1-[3-(dimethylamino)propyl]-(4-fluorophenyl)-1,3-dihydro-5-isobenzofurancarbonitrile; See U.S. Pat. No. 4,136,193; Christensen et al., *Eur. J Pharmacol.* 41:153, 1977; Dufour et al., *Int. Clin. Psychopharmacol.* 2:225, 1987; Timmerman et al., ibid., 239, each of which is incorporated herein by reference in its entirety); fluoxetine (N-methyl-3-(p-trifluoromethylphenoxy)-3-phenylpropylamine, marketed in the hydrochloride salt form and as the racemic mixture of its two isoforms; see, for example, U.S. Pat. No. 4,314,081; Robertson et al., *J. Med. Chem.* 31:1412, 1988, each of which is incorporated herein by reference); fluoxetine/olanzapine in combination;; fluvoxamine (5-methoxy-1-[4-(trifluoromethyl)phenyl]-1-pentanone O-(2-aminoethyl)oxime; See U.S. Pat. No. 4,085,225; Claassen et al., *Brit. J. Pharmacol.* 60:505, 1977; De Wilde et al., *J. Affective Disord.* 4:249, 1982; Benfield et al., *Drugs* 32:313, 1986, each of which is incorporated herein by reference in its entirety); paroxetine (trans-(−)-3-[(1,3-benzodioxol-5-yloxy)methyl]-4-(4-fluorophenyl)piperidine; See U.S. Pat. No. 3,912,743; U.S. Pat. No. 4,007,196; Lassen, *Eur. J Pharmacol.* 47:351, 1978; Hassan et al., *Brit. J. Clin. Pharmacol.* 19:705, 1985; Laursen et al., *Acta Psychiat. Scand.* 71:249, 1985; Battegay et al., *Neuropsychobiology* 13:31, 1985, each of which is incorporated herein by reference in its entirety); sertraline, (1S-cis)-4-(3,4-dichlorophenyl)-1,2,3,4-tetrahydro-N-methyl-1-naphthylamine hydrochloride; See U.S. Pat. No. 4,536,518, incorporated herein by reference in its entirety); escitalopram (see U.S. Pat. No. RE 34,712); and pharmaceutically acceptable salts thereof.

Suitable MAOIs for administering in combination with compounds of the present invention include: isocarboxazid, phenelzine, selegiline and tranylcypromine, and pharmaceutically acceptable salts thereof.

Suitable reversible MAOIs for administering in combination with compounds of the present invention include: moclobemide (4-chloro-N-[2-(4-morpholinyl)-ethyl]benzamide; See U.S. Pat. No. 4,210,754, incorporated herein by reference in its entirety), selegiline, and pharmaceutically acceptable salts thereof.

Suitable SNRIs for administering in combination with compounds of the present invention include venlafaxine (see U.S. Pat. No. 4,535,186, incorporated herein by reference in its entirety; see also U.S. Pat. Nos. 5,916,923, 6,274,171, 6,403,120, 6,419,958, 6,444,708, each of which is incorporated herein by reference in its entirety), and pharmaceutically acceptable salts and analogs, including the O-desmethylvenlafaxine succinate salt; milnacipran (N,N-diethyl-2-aminomethyl-1-phenylcyclopropanecarboxamide; see U.S. Pat. No. 4,478,836; Moret et al., *Neuropharmacology* 24:1211-19, 1985, each of which is incorporated herein by reference in its entirety); nefazodone (available from Bristol Myers Squibb and Dr. Reddy Labs Inc.); duloxetine; and pharmaceutically acceptable salts thereof.

Suitable CRF antagonists for administering in combination with compounds of the present invention include those compounds described in International Patent Specification Nos. WO 94/13643, WO 94/13644, WO 94/13661, WO 94/13676 and WO 94/13677.

Suitable atypical antidepressants for administering in combination with compounds of the present invention include: bupropion (Wellbutrin™; (.+−.)-1-(3-chlorophenyl)-2-[(1,1-dimethylethyl)amino]-1-propanone), lithium, nefazodone, trazodone and viloxazine, and pharmaceutically acceptable salts thereof. Another suitable atypical antidepressant is sibutramine.

Particular antidepressants for administering in combination with compounds of the present invention include, but are not limited to, adinazolam, alaproclate, alnespirone, amineptine, amitriptyline, amitriptyline/chlordiazepoxide combination, amoxapine, aprepitant, atipamezole, azamianserin, bazinaprine, befuraline, bifemelane, binodaline, bipenamol, brofaromine, buprorion, caroxazone, cericlamine, cianopramine, cimoxatone, citalopram, clemeprol, clomipramine, clovoxamine, dazepinil, deanol, demexiptiline, desipramine, O-desmethylvenlafaxine, dibenzepin, dothiepin, doxepin, droxidopa, duloxetine, elzasonan, enefexine, eptapirone, escitalopram, estazolam, etoperidone, femoxetine, fengabine, fezolamine, fluotracen, fluoxetine, fluvoxamine, gepirone, idazoxan, imipramine, indalpine, indeloxazine, iprindole, isocarboxazid, levoprotiline, litoxetine, lofepramine, maprotiline, medifoxamine, metapramine, metralindole, mianserin, milnacipran, minaprine, mirtazapine, moclobemide, montirelin, nebracetam, nefopam, nefozodine, nemititide, nialamide, nomifensine, norfluoxetine, nortriptyline, orotirelin, oxaflozane, paroxetine, pheneizine, pinazepam, pirlindone, pizotyline, protryptiline, reboxetine, ritanserin, robalzotan, rolipram, selegiline, sercloremine, sertraline, setiptiline, sibutramine, sulbutiamine, sulpiride, sunepitron, teniloxazine, thozalinone, thymoliberin, tianeptine, tiflucarbine, tofenacin, tofisopam, toloxatone, tomoxetine, tranylcypromine, trazodone, trimiprimine, venlafaxine, veralipride, vilazodone, viloxazine, viqualine, zimelidine and zometrapine, and pharmaceutically acceptable salts thereof, and St. John's wort herb, or Hypencuin perforatum, or extracts thereof.

Suitable classes of anti-anxiety agents for administering in combination with compounds of the present invention include $5\text{-HT}_{1A}$ agonists or antagonists, especially $5\text{-HT}_{1A}$ partial agonists, neurokinin recepter (NK) antagonists (e.g., saredutant and osanetant) and corticotropin releasing factor (CRF) antagonists. Suitable $5\text{-HT}_{1A}$ receptor agonists or antagonists that may be used in the present invention include, in particular, the $5\text{-HT}_{1A}$ receptor partial agonists buspirone, flesinoxan, gepirone and ipsapirone, and pharmaceutically acceptable salts thereof. An example of a compound with $5\text{-HT}_{1A}$ receptor antagonist/partial agonist activity is pindolol. new $5\text{HT}_{1A}$ agonists variza, alnespirone, gepirone, sunepitron, MKC242, vilazodone, eptapirone, and ORG12962 from Organon; new $5\text{HT}_{1A}$ antagonists such as robalzotan; new $5\text{-HT}_{1B}$ agonists such as elzasonan; new $5\text{HT}_{2}$ antagonists such as YM-992 (from Yamanouchi Pharmaceuticals) and nemifitide.

According to the present invention, the inventive combinations may be administered in conjunction with one or more other agents that is useful in treating depression or other mood disorders. Alternatively or additionally, inventive combinations may be administered with one or more other pharmaceutical agents active in treating any other symptom or medical condition present in the mammal that is related or unrelated to the depression or mood disorder being experienced by the mammal. Examples of such pharmaceutical agents include, for example, anti-angiogenic agents, anti-neoplastic agents, anti-diabetic agents, anti-infective agents, pain-relieving agents, anti-psychotic agents, gastrointestinal agents, etc., or combinations thereof. Other pharmaceutical agents useful in the practice of the present invention include, for example, adjunctive therapies typically used to enhance the effects of an antidepressant. Such adjunctive agents may include, for instance, mood stabilizers (e.g., lithium, valproic acid, carbamazepine, etc.); pindolol, stimulants (e.g., methylphenidate, dextroamphetamine, etc.); or thyroid augmenting agents (e.g., $T_3$); antipsychotics, anti-anxiety agents (e.g., benzodiazepines), and/or agents that relieve sexual dysfunction (e.g., buspirone, which also has anti-anxiety effects; dopaminergic agents such as amantadine, pramipexole, bupropion, etc.).

As $5\text{-HT}_{2C}$ modulators, compounds of the present invention are useful for treating a variety of disorders. Such disorders include premenstrual syndrome (PMS), premenstrual dysphoric disorder (PMDD), motion or motor disorders such as Parkinson's disease; chronic fatigue syndrome, anorexia nervosa, disorders of sleep (e.g., sleep apnea), and mutism.

Premenstrual dysphoric disorder, or PMDD, is a severe form of PMS. Like PMS, PMDD typically occurs the week before the onset of menstruation and disappears a few days after. PMDD is characterized by severe monthly mood swings and physical symptoms that interfere with everyday life, especially a woman's relationships with her family and friends. PMDD symptoms go far beyond what are considered manageable or normal premenstrual symptoms.

PMDD is a combination of symptoms that may include irritability, depressed mood, anxiety, sleep disturbance, difficulty concentrating, angry outbursts, breast tenderness and bloating. The diagnostic criteria emphasize symptoms of depressed mood, anxiety, mood swings or irritability. The condition affects up to one in 20 American women who have regular menstrual periods. According to another embodiment, the present invention provides a method for treating one or more symptoms associated with PMDD.

Selective serotonin reuptake inhibitors (SSRIs) are the current preferred method for treating symptoms associated with PMDD. According to another aspect, the present invention provides a method for treating PMDD, or one or more symptoms associated with PMDD, by administering a compound of formula I in combination with an SSRI. In certain embodiments, the SSRI is fluoxetine, venlafaxine, paroxetine, duloxetine, or sertraline.

According to another embodiment, compounds of the present invention are useful for treating a variety of eating disorders. In certain embodiments, the eating disorder is hyperphagia, bulimia or anorexia nervosa. In certain embodiments, compounds of the present invention are useful for treating gastrointestinal disorders, such as malfunction of gastrointestinal motility or intestinal propulsion. Compounds of the present invention are also useful in connection with weight loss or control (e.g., reduction in calorie or food intake, and/or appetite suppression). Such methods are particularly useful for treating obesity with its consequent comorbidities including diabetes insipidus, Type II diabetes, cardiovascular disease, hypertension, hyperlipidemia, stroke, osteoarthritis, sleep apnea, gall bladder disease, gout, some cancers, some infertility, and early mortality.

In certain embodiments, compounds of the present invention are administered in combination with one or more anti-obesity agents. Such anti-obesity agents are known in the art and include apolipoprotein-B secretion/microsomal triglyceride transfer protein (apo-B/MTP) inhibitors, 11β-hydroxy steroid dehydrogenase-1 (11(β-HSD type 1) inhibitors, $PYY_{3\text{-}36}$ and analogs thereof, MCR-4 agonists, cholecystokinin-A (CCK-A) agonists, monoamine reuptake inhibitors (such as sibutramine), sympathomimetic agents, R3 adrenergic receptor agonists, dopamine agonists (such as bromocriptine), melanocyte-stimulating hormone receptor analogs, cannabinoid 1 receptor antagonists (e.g., rimonabant), melanin concentrating hormone antagonists, leptins (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y receptor antagonists, thyromimetic agents, dehydroepiandrosterone or an analog thereof, glucocorticoid receptor agonists or antagonists, orexin receptor antagonists, urocortin binding protein antagonists, glucagon-like peptide-1 receptor agonists, ciliary neurotrophic factors (such as Axokine$^{TA}$), human agouti-related proteins (AGRP), ghrelin receptor antagonists, histamine 3 receptor antagonists or inverse agonists, and neuromedin U receptor agonists.

In other embodiments, a compound of the present invention is administered in combination with an anti-obesity agent selected from orlistat, sibutramine, bromocriptine, ephedrine, leptin, rimonabant, pseudoephedrine, PYY3.36 or an analog thereof, and 2-oxo-N-(5-phenyipyrazinyl) spiro-[isobenzofuran-1(3H),4'-piperidine]-1'-carboxamide. According to another aspect of the invention, a compound of the present invention is administered in combination with an anti-obesity agent in conjunction with typical treatments for obesity such as exercise and a sensible diet.

According to another embodiment, a compound of the present invention is administered in combination with one or more agents for treating diabetes and associated conditions. In certain embodiments, a compound of the present invention is administered in combination with one or more such agents including insulin and insulin analogs (e.g., LysPro Insulin); GLP-1 (7-37) (insulinotropin) and GLP-1 (7-36)-$NH_2$; sulfonylureas and analogs thereof: chlorpropamide, glibenclamide, tolbutamide, tolazamide, acetohexamide, Glypizide®, glimepiride, repaglinide, meglitinide; biguanides: metformin, phenformin, buformin; $^{<<}$2-antagonists and imidazolines: midaglizole, isaglidole, deriglidole, idazoxan, efaroxan, fluparoxan; other insulin secretagogues: linogliride, A-4166; glitazones: ciglitazone, Actos® (pioglitazone), englitazone, troglitazone, darglitazone, Avandia® (BRL49653); fatty acid oxidation inhibitors: clomoxir, etomoxir; glucosidase inhibitors: acarbose, miglitol, emiglitate, voglibose, MDL-25,637, camiglibose, MDL-73,945; 13-agonists: BRL 35135, BRL 37344, RO 16-8714, ICI D7114, CL 316,243; or phosphodiesterase inhibitors: L-386, 398.

In other embodiments, a compound of the present invention is administered in combination with one or more lipid-lowering agents: benfluorex: vanadate and vanadium complexes (e.g., Nagiivan®) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin"), AC 2993, nateglinide, aldose reductase inhibitors (e.g., zopolrestat), glycogen phosphorylasc inhibitors, sorbitol dehydrogenase inhibitors, sodium-hydrogen exchanger type 1 (NNE-1) inhibitors and/or cholesterol biosynthesis inhibitors or cholesterol absorption inhibitors, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, or an anti-oxidant. In other embodiments, a compound of the present invention is administered in combination with one or more naturally occurring compounds that acts to lower plasma cholesterol levels. Such naturally occurring compounds are commonly referred to as nutraceuticals and include, for example, garlic extract, *Hoodia* plant extracts, and niacin.

In certain embodiments, compounds of the present invention are useful for inducing, assisting or maintaining desirable bladder control in a mammal. The methods are particularly useful for treating a mammal that is experiencing or susceptible to bladder instability or urinary incontinence. Inventive methods include prevention, treatment or inhibition of bladder-related urinary conditions and bladder instability, including idiopathic bladder instability, nocturnal enuresis, nocturia, voiding dysfunction and urinary incontinence (including, for example, stress incontinence, urge incontinence, and/or mixed incontinence). Also treatable or preventable by administration of a compound of this invention is bladder instability secondary to prostate hypertrophy, as is a method for enhancing urethral tone and reducing undesirable urine leakage even in an otherwise healthy person. For example, the inventive methods are applicable to alleviating urine leakage often occurring in women during the first year after childbirth.

In other embodiments, the present compounds are useful for treating urine retention or detrusor sphinctor dyssynergia. Patients suffering from urine retention include those suffering from spinal cord injuries or male patients with benign prostatic hyperplasia.

According to the present invention, a compounds of the present invention is also useful in promoting the temporary delay of urination whenever desirable. Such compounds may be utilized in accordance with the present invention to stabilize the bladder in any applicable context. Inventive methods therefore may be utilized to allow a recipient to control the urgency and frequency of urination.

In some embodiments of the invention, compounds of the present invention are administered to a mammal in need thereof for the treatment, prevention, inhibition and/or amelioration of urge urinary incontinence (also known as bladder instability, neurogenic bladder, voiding dysfunction, hyperactive bladder, detrusor overactivity, detrusor hyperreflexia or uninhibited bladder) or mixed urinary incontinence. Inventive uses include, but are not limited to, those for bladder activities and instabilities in which the urinary urgency is associated with prostatitis, prostatic hypertrophy, interstitial cystitis, urinary tract infections or vaginitis. The methods of this invention may also be used to assist in inhibition or correction of the conditions of Frequency-Urgency Syndrome, and lazy bladder, also known as infrequent voiding syndrome.

Compounds of the present invention may also be used to treat, prevent, inhibit, or limit the urinary incontinence, urinary instability or urinary urgency associated with or resulting from administrations of other medications, including diuretics, vasopressin antagonists, anticholinergic agents, sedatives or hypnotic agents, narcotics, alpha-adrenergic agonists, alpha-adrenergic antagonists, or calcium channel blockers.

Compounds of the present invention are useful for inducing or assisting in urinary bladder control or preventing or treating the maladies described herein in humans in need of such relief, including adult and pediatric uses. They may also be utilized for veterinary applications, particularly including canine and feline bladder control methods. If desired, the methods herein may also be used with farm animals, such as ovine, bovine, porcine and equine breeds.

According to the present invention, compounds of the present invention may be administered alone to modulate bladder activity, or alternatively may be administered in combination with (whether simultaneously or sequentially) one or more other pharmaceutical agents useful in the modulation of bladder activity. Alternatively or additionally, the compounds of the present invention may be administered in combination with one or more other pharmaceutical agents useful in the treatment or prevention of one or more other symptoms, disorders, or diseases suffered by the individual in need of bladder activity modulation.

Other pharmaceutical agents useful in the modulation of bladder activity, and particularly for treatment, prevention, inhibition, and/or amelioration of urinary incontinence, include, for example, desmopressin acetate (available as DDAVP® Nasal Spray and DDAVP® tablets from Aventis Pharmaceuticals), as well as a desmopressin acetate rhinal tube (available from Ferring Pharmaceuticals Inc.). Other products include, for example, tolterodine tartrate (available as Detroltm tablets from Pharmacia & Upjohn), oxybutinin chloride (available in the form of Ditropan® tablets and syrup and Ditropan XL® extended release tablets from ALZA Pharmaceuticals), propanthaline bromide (available in tablet form from Roxane Laboratories, Inc.), hyoscyamine and hyoscyamine sulfate (available, respectively, as Cystopaz® tablets and Cystopaz-M® timed release capsules from PolyMedica Pharmaceuticals (U.S.A.), Inc.), hyoscyamine hydrobromide, flavoxate HCl (available in Urispas® 100 mg tablets from ALZA Pharmaceuticals), imipramine HCl (available in 10 mg, 25 mg and 50 mg tablets from Geneva Pharmaceuticals, Inc.), phenylpropanolamine, midodrine HCl (available in 2.5 mg and 5 mg Proamatine® tablets from Shire US Inc.), phenoxybenzamine HCl (available as Dibenzyline® capsules from WellSpring Pharmaceuticals Corporation), and prazosin HCl (available in Minipress® capsules from Pfizer Inc.). Each of these medicaments may be administered in the pharmaceutically effective amounts and regimens known in the art, including those listed in the Physicians' Desk Reference, 55 Edition, 2001, published by Medical Economics Company, Inc. at Monvale, N.J. 07645-1742, the relevant portions of which are incorporated herein by reference.

Yet other pharmaceutical agents that can act to modulate bladder activity include, for example, other regulators of the $5HT_{2C}$ receptor. For example, United States Patent Application 2004/0235856 (previously incorporated herein by reference in its entirety) describes a variety of $5HT_{2C}$ receptor modulators that are useful in accordance with the practice of the present invention. Additional $5HT_{2C}$ agonists are exemplified in Bishop et al., *Expert Opin. Ther. Patent* 13:1691-1705, 2003, the entire contents of which are incorporated herein by reference.

Still other pharmaceutical agents that can act to modulate bladder activity include, for example, modulators of one or more KCNQ potassium channels. In some embodiments of the present invention, compounds of the present invention are administered in conjunction with one or more agonists of KCNQ 2/3 or KCNQ3/5. Such KCNQ modulators include, for example, compounds described in U.S. Pat. No. 5,384,330 and those described in U.S. Pat. No. 5,565,483, as well as those described in United States Patent Application Number 2002/0183395; and United States Patent Application Number 2004/0029949. The entire contents of each of these patents and patent applications is incorporated herein by reference. In some embodiments of the present invention, compounds of the present invention are administered with retigabine.

In some embodiments of the present invention, compounds of the present invention are administered in conjunction with one or more compounds which act as vasopressin agonists including, but not limited to those described in U.S. Pat. No. 6,194,407 (Failli et al.), U.S. Pat. No. 6,090,803 (Failli et al.), U.S. Pat. No. 6,096,736 (Ogawa et al.), and U.S. Pat. No. 6,096,735 (Ogawa et al.).

In general, it will often be desirable in accordance with the present invention to administer one or more compounds of the present invention in conjunction with one or more alpha-adrenergic receptor agonists and/or one or more other sympathomimetic drugs.

According to the present invention, compounds of formula I may be used to treat, prevent, or alleviate dependence, withdrawal, or symptoms thereof for any of a variety of substances including, for example, recreational substances (e.g., alcohol, tobacco [for example, nicotine]), pharmacologic agents (e.g., pain relievers [for example, Vicodin®, Lortab®, Lorcet®, Percocet®, Percodan®, Tylox®, Hydrocodone, OxyContin®, methadone, Tramadol, etc], tranquilizers, stimulants, or sedatives), and illicit drugs (e.g., marijuana, heroine, cocaine, ecstasy, LSD, PCP, methamphetamine, etc.).

The term "substance abuse", as used herein, may be defined with reference to criteria set form in the *Diagnostic and Statistical Manual of Mental Disorders*, $4^{th}$ Ed. (1994) ("DSM-IV"), which was prepared by the Task Force on Nomenclature and Statistics of the American Psychiatric Association. A feature of substance abuse is a maladaptive pattern of substance use manifested by recurrent and significant adverse consequences related to the repeated use of substances. As recited in the DSM-IV, substance abuse is defined as maladaptive pattern of substance abuse leading to clinicalyl significant impairment or distress, as manifested by one (or more) of the following, occurring within a 12-month period: (1) recurrent substance use resulting in a failure to fulfill major role obligations at work, school, or home; (2) recurrent substance use in situations in which it is physically hazardous; (3) recurrent substance-related legal problems; and (4) continued substance use despite having persistent or recurrent social or interpersonal problems cause or exacerbated by the effects of the substance. In addition, the DMS-IV requires that the symptoms of substance abuse do not meet the criteria for substance dependence.

The term "substance dependence", as used herein, may be defined with reference to criteria set form in the *Diagnostic and Statistical Manual of Mental Disorders*, $4^{th}$ Ed. (1994) ("DSM-IV"), which was prepared by the Task Force on Nomenclature and Statistics of the American Psychiatric Association. The criteria for substance dependence set forth in DSM-IV is a pattern of substance use, leading to clinically significant impairment or distress as manifested by at least three selected from the following group, occurring at any time within the same twelve month period: (1) tolerance as defined by either (a) a need for substantially increased amounts of the substance to achieve the desired effect; or (b) substantially diminished effect with continued use of the same amount of the substance; (2) withdrawal, as demonstrated by either (a) the characteristic withdrawal syndrome for the specific substance; or (b) the same, or a closely related substance is taken to relieve or avoid withdrawal symptoms; (3) the substance is often taken in larger amounts or over a longer period then was intended; (4) there is a persistent desire or unsuccessful efforts to cut down or control substance use; (5) a great deal of time is spent in activities to obtain the substance, use the substance, or recover from its effects; (6) important social, occupational or recreational activities are given up or reduced because of substance use; and (7) the substance use is continued despite knowledge of having a persistent or recurrent physical or psychological problem that is likely to have been caused or exacerbated by the substance. Substance dependence can be with physiological dependence; that is evidence of tolerance or withdrawal is present, or without physiological dependence, where no evidence of tolerance or withdrawal is present. Four of the conditions set forth in DSM-IV include remission. These types of remission are based on the interval of time that has elapsed since the cessation of dependencies and whether there is continued presence of one or more of the symptoms included in the criteria for dependencies.

In certain embodiments, compounds of the present invention are useful for treating alcoholism (e.g., alcohol abuse, addiction and/or dependence including treatment for abstinence, craving reduction and relapse prevention of alcohol intake) and/or tobacco abuse (e.g., smoking addiction, cessation and/or dependence including treatment for craving reduction and relapse prevention of tobacco smoking).

In evaluating substance abuse in accordance with the present invention, reference may be made, for example, to the National Survey on Drug Use and Health (NSDUH), which obtains information on nine different categories of illicit drug use: marijuana, cocaine, heroin, hallucinogens, inhalants, and nonmedical use of prescription-type pain relievers, tranquilizers, stimulants, and sedatives. In these categories, hashish is included with marijuana, and crack is considered a form of cocaine. Several drugs are grouped under the hallucinogens category, including LSD, PCP, peyote, mescaline, mushrooms, and "Ecstasy" (MDMA). Inhalants include a variety of substances, such as amyl nitrite, cleaning fluids, gasoline, paint, and glue. The four categories of prescription-type drugs (pain relievers, tranquilizers, stimulants, and sedatives) cover numerous drugs available through prescriptions and sometimes illegally "on the street." Methamphetamine is considered a type of stimulant. Respondents are asked to report only uses of drugs that were not prescribed for them or drugs they took only for the experience or feeling they caused. Over-the-counter drugs and legitimate uses of prescription drugs are not included. NSDUH reports combine the four prescription-type drug groups into a category referred to as "any psychotherapeutics."

The NSDUH categorizes alcohol abuse through use of questions about the frequency of the consumption of alcoholic beverages, such as beer, wine, whiskey, brandy, and mixed drinks. An extensive list of examples of the kinds of beverages covered is given to respondents prior to the question administration. A "drink" is defined as a can or bottle of beer, a glass of wine or a wine cooler, a shot of liquor, or a mixed drink with liquor in it. Times when the respondent only had a sip or two from a drink are not considered as consumption. For this report, estimates for the prevalence of alcohol use are reported primarily at three levels defined for both males and females and for all ages as follows:

Current use—At least one drink in the past 30 days (includes binge and heavy use).
Binge use—Five or more drinks on the same occasion at least once in the past 30 days (includes heavy use).
Heavy use—Five or more drinks on the same occasion on at least 5 different days in the past 30 days The NSDUH also characterizes the use of tobacco products, including cigarettes, chewing tobacco, snuff, cigars, and pipe tobacco. For analytic purposes, data for chewing tobacco and snuff are combined as "smokeless tobacco." Cigarette use is defined as smoking "part or all of a cigarette." Questions to determine nicotine dependence among current cigarette smokers also are included in NSDUH. Nicotine dependence is based on criteria from the Nicotine Dependence Syndrome Scale (NDSS) or the Fagerstrom Test of Nicotine Dependence (FTND).

In other embodiments, compounds of the present invention are useful for treating withdrawal from drug addiction including addiction to nicotine, alcohol, and other substances of abuse. Individuals often suffer the symptoms of nicotine withdrawal as a consequence of the discontinued use of tobacco in any form, including, but not limited to smoking of cigarette, cigar, or pipe tobacco, or the oral or intranasal ingestion of tobacco or chewing tobacco. Such oral or intranasal tobacco includes, but is not limited to snuff and chewing tobacco. The cessation of nicotine use or reduction in the amount of nicotine use, is often followed within 24 hours by symptoms including dysphoric, depressed mood; light-headedness; insomnia; irritability, frustration or anger; anxiety; nervous tremor; difficulty concentrating; restlessness; decreased heart rate; increased appetite or weight gain; and the craving for tobacco or nicotine. These symptoms often cause clinically significant distress or impairment in social, occupational, or other important areas of functioning.

The discontinued or reduction in administration of an opioid, typically self-administration, through injection or orally, through smoking or intranasal ingestion, often results in the presence of a characteristic opioid withdrawal condition. This withdrawal condition can also be precipitated by administration of an opioid antagonist such as naloxone or naltrexone after opioid use. Opioid withdrawal is characterized by symptoms that are generally opposite to the opioid agonist effects. These withdrawal symptoms may include anxiety; restlessness; muscle aches, often in the back and legs; craving for opioids; irritability and increased sensitivity to pain; dysphoric mood; nausea or vomiting; lacrimation; rhinorrhoea; papillary dilation; piloerection; sweating; diarrhea; yawning; fever; and insomnia. When dependence is on short-acting opioids, such as heroin, withdrawal symptoms usually occur within 6-24 hours after the last dose, while with longer-acting opioids, such as methadone, symptoms may take 2-4 days to emerge. These symptoms often cause clinically significant distress or impairment in social, occupational or other important areas of functioning. The present invention is most preferably used to alleviate one or more symptoms attributed to opioid withdrawal when such symptoms are not due to a general medical condition and are not better accounted for by another medical disorder.

The discontinued or reduction in use of ethanol (ethanol containing beverages) results in the onset of ethanol withdrawal conditions. Ethanol withdrawal conditions are characterized by symptoms that begin when blood concentrations of ethanol decline sharply, within 4 to 12 hours after ethanol use has been stopped or reduced. These ethanol withdrawal symptoms include craving for ethanol; autonomic hyperactivity (such as sweating or pulse rate greater than 100); hand tremor; insomnia; nausea; vomiting; transient visual, tactile, or auditory hallucinations or illusions; psychomotor agitation; anxiety; and grand mal seizures. These symptoms often cause clinically significant distress or impairment in social, occupational, or other important areas of functioning. The present invention is most preferably used to alleviate one or more symptoms attributed to ethanol withdrawal when such symptoms are not due to a general medical condition and are not better accounted for by another medical disorder.

According to another embodiment, a compound of the present invention is administered in combination with one or more agents useful for treating substance abuse. In certain embodiments, a compound of the present invention is administered in combination with one or more agents to treat tobacco abuse. Such agents include nicotine receptor partial agonists bupropion hypochloride (Zyban™) and nicotine replacement therapies.

According to yet another embodiment, a compound of the present invention is administered in combination with one or more agents to treat alcoholism, such as opioid antagonists (e.g., naltrexone, ReVia™), nalmefene, disulfiram (Antabuse™), and acamprosate (Campral™).

In certain embodiments, a compound is administered in combination with one or more agents for reducing alcohol withdrawal symptoms such as benzodiazepines, beta-blockers, clonidine, carbamazepine, pregabalin, and gabapentin (Neurontin™). In other embodiments of the invention, therapy utilizing compounds of the present invention is administered concomitantly with, in connection with, and/or subsequent to an educational and/or behavioral modification program to enhance continued abstinence from substance dependence or abuse. The method of the present invention may be particularly useful in treating symptoms of withdrawal often observed in rehabilitation or other treatment programs. Therefore, the programs can be more effective by focusing on educational and behavioral modification goals, further reducing the incidence of program non-completion.

In certain embodiments, compounds of the present invention are useful for treating one or more intellectual deficit disorders comprising administering a compound of the present invention. In other embodiments, such intellectual deficit disorders include dementia, such as dementia of aging, vascular dementia, mild cognitive impairment, age-related cognitive decline, and mild neurocognitive disorder; Alzheimer's disease, and memory deficit, attention deficit disorders (ADD, also known as Attention Deficit Hyperactivity Disorder or ADHD) in both children and adults. In certain embodiments, the present invention provides a method of treating ADD and/or ADHD in a pediatric patient comprising administering to said patient a compound of formula I or pharmaceutical composition thereof.

In other embodiments, the present invention provides a method of treating one or more cognition disorders. According to another aspect, the cognition disorder is a learning disorder. Such learning disorders are known in the art and include autism, dyslexia, Asperger's syndrome, a neurobiological disorder similar to autism and characterized by serious deficits in social and communication skills; specific learning disability, a disorder in one or more of the basic psychological processes involved in understanding or in using spoken or written language, which may manifest itself in an imperfect ability to listen, think, speak, read, write, spell or to do mathematical calculations; dysgraphia, a disorder that causes difficulty with forming letters or writing within a defined space; dyscalculia, a disorder that causes people to have problems doing arithmetic and grasping mathematical concepts; dyspraxia, a problem with the body's system of motion that interferes with a person's ability to make a controlled or coordinated physical response in a given situation; visual perceptual deficit, difficulty receiving and/or processing accurate information from the sense of sight, although there is nothing wrong with vision; and auditory perceptual deficit, difficulty receiving accurate information through auditory means, even though there is no problem with hearing.

In certain embodiments, the present invention provides a method for treating one or more impulsivity disorders (e.g. borderline personality disorder), disruptive behavior disorders, or impulse control disorders. In certain embodiments, the present invention provides a method for treating Tourette's syndrome (TS), an inherited, neurological disorder characterized by repeated and involuntary body movements (tics) and/or uncontrollable vocal sounds.

According to another aspect, the present invention provides a method for treating one or more behavioral addictions and addictive disorders. Behavioral addictions and addictive disorders result from the intoxication one senses from the release of brain chemicals (e.g., serotonin, adrenaline, epinepherine, etc.) during certain activities. Such disorders are known in the art and include gambling, sex addiction, eating disorders, spending addiction, rage/anger, workaholism, exercise addiction, risk taking addictions, and perfectionism to name a few.

In certain embodiments, a compound of the present invention is administered in combination with one or more cognitive improvement agents. Such agents are well known in the art and include donepezil hydrochloride (Aircept™) and other acetylcholinesterase inhibitors; galantamine, neuroprotective agents (e.g., memantine); ADD/ADHD agents (e.g., methylphenidate (Ritalin$^{Tm}$"), atomoxetine (Strattera™), methylphenidate, sustained release (Concerta™) and amphetamine/dextroamphetamine (Adderall™).

According to another aspect, the present invention provides a method for treating sexual dysfunction comprising administering a compound of the present invention. In certain embodiments, the sexual dysfunction is associated with a depressive disorder. In other embodiments, the sexual dysfunction is associated with treatment of a disorder by administration of a serotonin reuptake inhibitor. Compounds of the present invention are useful for treating sexual dysfunction in the male and in the female. Such disorders include male erectile dysfunction (MED) and female sexual dysfunction (FSD), e.g. female sexual arousal disorder (FSAD).

In other embodiments, the present invention provides a method for treating one or more disorders associated with sexual dysfunction including: HSDD, characterized by a deficiency, or absence of, sexual fantasies and desire for sexual activity; FSAD, characterized by a persistent or recurrent inability to attain, or to maintain until completion of the sexual activity, an adequate lubrication-swelling response of sexual excitement; FOD characterized by persistent or recurrent delay in, or absence of, orgasm following a normal sexual excitement phase; Sexual Pain Disorders such as dyspareunia and vaginismus; and/or HSDD characterized by a woman who has no or little desire to be sexual, and has no or few sexual thoughts or fantasies.

According to another embodiment, a compound of the present invention is administered in combination with one or more agents for treating male sexual dysfunction (e.g., male erectile dysfunction). Such agents are known in the art and include a dopaminergic agent (e.g. D2, D3 or D4 agonists and apomorphine); an NPY (neuropeptide Y) (preferably an NPY-1 and/or NPY-5 inhibitor); a melanocortin receptor agonist or modulator or melanocortin enhancer; an NEP inhibitor; a PDE inhibitor (preferably, a cGMP PDE-5 inhibitor); a bombesin receptor antagonist or modulator, and a soluble secreted endopeptidase inhibitor (SEPi). In certain embodiments, a compound of the present invention is administered in combination with one or more agents for treating male sexual dysfunction such as alprostadil or sildenafil.

According to yet another embodiment, a compound of the present invention is administered in combination with one or more agents for treating female sexual dysfunction. Such agents are known in the art and include estrogen receptor modulators (e.g., estrogen agonists and/or estrogen antagonists); testosterone replacement agents, testosternone (Tostrelle), dihydrotestosterone, dehydroepiandrosterone (DHEA), a testosterone implant; eg dehydroandrostendione, estrogen, estrogen, medroxyprogesterone, medroxyprogesterone acetate (MPA), a combination of estrogen and a methyl testosterone hormone replacement therapy agent; Premarin, Cenestin, Oestrofeminal, Equin, Estrace, Estrofem, Elleste Solo, Estring, Eastraderm TTS, Eastraderm Matrix, Dermestril, Premphase, Preempro, Prempak, Premique, Estratest, Estratest HS, Tibolone, a dopaminergic agent; eg apomorphine or a selective D2, D3 or D2/D3 agonist such as, pramipexole and ropirinol, a NPY (neuropeptide Y) inhibito; eg a NPY (neuropeptide Y) inhibitor such as a NPY1 or NPY5 inhibitor, preferably NPY1 inhibitor, a melanocortin receptor modulator or a melanocortin enhancer; eg melanotan II, PT-14, PT-141, a NEP (neutral endopeptidase) inhibitor; a PDE (phosphodiesterase) inhibitor; eg sildenafil, and/or a bombesin receptor modulator.

According to the present invention, compounds of the present invention are useful for treating any of a variety of different types of pain experienced by mammals, such as humans. For example, the compounds of the present invention may be used to treat treating acute pain (short duration) or chronic pain (regularly reoccurring or persistent), whether centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as bum pain, or headaches such as migraines or tension headaches, or combinations of these pains. One skilled in the art will recognize that these pains may overlap one another. For example, a pain caused by inflammation may also be visceral or musculoskeletal in nature.

In one embodiment of the present invention, one or more compounds of the present invention is/are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromylagia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, sickle cell anemia, autoimmune disorders, multiple sclerosis, or inflammation such as osteoarthritis or rheumatoid arthritis.

In some embodiments, the compounds of the present invention are used to treat chronic pain that is neuropathic pain, visceral pain, musculoskeletal pain, bony pain, headache, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. Inventive treatment methods further include treatments in which the neuropathic pain is a condition secondary to metastatic infiltration, adiposis dolorosa, bums or central pain conditions related to thalamic conditions.

Neuropathic pains described above may also be, in some circumstances, classified as "painful small fiber neuropathies" such as idiopathic small-fiber painful sensory neuropathy, or "painful large fiber neuropathies" such as demylinating neuropathy or axonal neuropathy, or combinations thereof. Such neuropathies are described in more detail, for example, in the J. Mendell et al., *N. Engl. J. Med.* 2003, 348:1243-1255, which is hereby incorporated by reference in its entirety.

In another embodiment, the compounds useful in the present invention may be administered to totally or partially inhibit a neuropathic pain condition from developing. For example, compounds of the present invention may be administered to a mammal who is at risk for developing a neuropathic pain condition such as a mammal who has contracted shingles or a mammal who is being treated for cancer.

In one embodiment, the compounds useful in the present invention may be administered prior to or during a surgical procedure to partially or totally inhibit development of pain associated with the surgical procedure.

As mentioned previously, the methods of the present invention may be used to treat pain that is somatic and/or visceral in nature. For example, somatic pain that can be treated in accordance with the methods of the present invention includes pain associated with structural or soft tissue injury experienced during surgery, dental procedures, bums, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, chronic pain to be treated in accordance with the present invention may be with or without peripheral or central sensitization.

The present invention also provides use of the compounds of the present invention to treat acute and/or chronic pains associated with female conditions, which may also be referred to as female-specific pain. Such types of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

In certain embodiments, a compound of the present invention is administered in combination with a pain relieving agent. Examples of pain relieving agents that may be administered with compounds of the present invention include, but are not limited to, analgesics such as non-narcotic analgesics or narcotic analgesics; anti-inflammatory agents such as non-steroidal anti-inflammatory agents (NSAIDs), steroids or anti-rheumatic agents; migraine preparations such as beta adrenergic blocking agents, ergot derivatives, or isomeptene; tricyclic antidepressants such as amitryptyline, desipramine, or imipramine; anti-epileptics such as gabapentin, carbamazepine, topiramate, sodium valproate or phenytoin; $\alpha_2$ agonists; or selective serotonin reuptake inhibitors/selective norepinepherine uptake inhibitors, or combinations thereof.

One skilled in the art will recognize that some agents described herein act to relieve multiple conditions such as pain and inflammation, while other agents may just relieve one symptom such as pain. A specific example of an agent having multiple properties is aspirin, where aspirin is anti-inflammatory when given in high doses, but at lower doses is just an analgesic. The pain relieving agent may include any combination of the aforementioned agents, for example, the pain relieving agent may be a non-narcotic analgesic in combination with a narcotic analgesic.

Non-narcotic analgesics useful in the practice of the present invention include, for example, salicylates such as aspirin, ibuprofen (Motrin®, Advil®), ketoprofen (Orudis®), naproxen (Naprosyn®), acetaminophen, indomethacin or combinations thereof. Examples of narcotic analgesic agents that may be used in combination with compounds of the present invention include opioid analgesics such as fentenyl, sufentanil, morphine, hydromorphone, codeine, oxycodone, buprenorphine or pharmaceutically acceptable salts thereof or combinations thereof. Examples of anti-inflammatory agents that may be used in combination with compounds of the present invention include but are not limited to aspirin; ibuprofen; ketoprofen; naproxen; etodolac (Lodine®); COX-2 inhibitors such as celecoxib (Celebrex®), rofecoxib (Vioxx®), valdecoxib (Bextra®), parecoxib, etoricoxib (MK663), deracoxib, 2-(4-ethoxy-phenyl)-3-(4-methanesulfonyl-phenyl)-pyrazolo[1,5-b] pyridazine, 4-(2-oxo-3-phenyl-2,3-dihydrooxazol-4-yl)benzenesulfonamide, darbufelone, flosulide, 4-(4-cyclohexyl-2-methyl-5-oxazolyl)-2-fluorobenzenesulfonamide), meloxicam, nimesulide, 1-Methylsulfonyl-4-(1,1-dimethyl-4-(4-fluorophenyl)cyclopenta-2,4-dien-3-yl)benzene, 4-(1,5-Dihydro-6-fluoro-7-methoxy-3-(trifluoromethyl)-(2)-benzothiopyrano(4,3-c)pyrazol-1-yl)benzenesulfonamide, 4,4-dimethyl-2-phenyl-3-(4-methylsulfonyl)phenyl)cyclobutenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, or their physiologically acceptable salts, esters or solvates; sulindac (Clinoril®); diclofenac (Voltaren®); piroxicam (Feldene®); diflunisal (Dolobid®), nabumetone (Relefen®), oxaprozin (Daypro®), indomethacin (Indocin®); or steroids such as Pediaped® prednisolone sodium phosphate oral solution, Solu-Medrol® methylprednisolone sodium succinate for injection, Prelone® brand prednisolone syrup.

Further examples of anti-inflammatory agents that may be used for treating pain, for example associated with rheumatoid arthritis, in accordance with the present invention include naproxen, which is commercially available in the form of EC-Naprosyn® delayed release tablets, Naprosyn®, Anaprox® and Anaprox® DS tablets and Naprosyn® suspension from Roche Labs, Celebrex® brand of celecoxib tablets, Vioxx® brand of rofecoxib, Celestone® brand of betamethasone, Cupramine® brand penicillamine capsules, Depen® brand titratable penicillamine tablets, Depo-Medrol® brand of methylprednisolone acetate injectable suspension, Arava™ leflunomide tablets, Azulfidine EN-tabs® brand of sulfasalazine delayed release tablets, Feldene® brand piroxicam capsules, Cataflam® diclofenac potassium tablets, Voltaren® diclofenac sodium delayed release tablets, Voltaren®-XR diclofenac sodium extended release tablets, or Enbrel® etanerecept products.

Examples of yet other agents used to treat inflammations, especially rheumatoid arthritis, include immunosuppressants such as Gengraf™ brand cyclosporine capsules, Neoral® brand cyclosporine capsules or oral solution, or Imuran® brand azathioprine tablets or IV injection; Indocin® brand indomethacin capsules, oral suspension or suppositories; Plaquenil® brand hydroxychloroquine sulfate; or Remicade® infliximab recombinant for IV injection; or gold compounds such as auranofin or Myochrisyine® gold sodium thiomalate injection.

As $5\text{-HT}_{2C}$ modulators, compounds of the present invention are useful for treating a variety of disorders. Such disorders include premenstrual syndrome, motion or motor disorders such as Parkinson's disease and epilepsy; migraines, chronic fatigue syndrome, anorexia nervosa, disorders of sleep (e.g., sleep apnea), and mutism.

In other embodiments, compounds of the present invention are useful for treating one or more central nervous system deficiencies associated, for example, with trauma, stroke, and spinal cord injuries, neurodegenerative diseases or toxic or infective CNS diseases (e.g., encephalitis or meningitis), or Parkinson's disease. The compounds of the present invention can therefore be used to improve or inhibit further degradation of central nervous system activity during or following the malady or trauma in question. Included in these improvements are maintenance or improvement in motor and motility skills, control, coordination and strength.

5. Pharmaceutically Acceptable Compositions

In other embodiments, the invention relates to compositions comprising at least one compound of formula I or VII, or a pharmaceutically acceptable salt thereof, and one or more pharmaceutically acceptable carriers, excipients, or diluents. Such compositions include pharmaceutical compositions for treating or controlling disease states or conditions of the central nervous system. In certain embodiments, the compositions comprise mixtures of one or more compounds of formula I or VII.

In certain embodiments, the invention relates to compositions comprising at least one compound of formula I or VII, or a pharmaceutically acceptable salt thereof, and one or more pharmaceutically acceptable carriers, excipients, or diluents. Such compositions are prepared in accordance with acceptable pharmaceutical procedures, such as, for example, those described in *Remingtons Pharmaceutical Sciences,* 17th edition, ed. Alfonoso R. Gennaro, Mack Publishing Company, Easton, Pa. (1985), which is incorporated herein by reference in its entirety. Pharmaceutically acceptable carriers are those carriers that are compatible with the other ingredients in the formulation and are biologically acceptable.

The compounds of formula I or VII can be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of formula I or VII can be administered rectally or vaginally in the form of a conventional suppository. For administration by intranasal or intrabronchial inhalation or insufflation, the compounds of formula I or VII can be formulated into an aqueous or partially aqueous solution, which can then be utilized in the form of an aerosol. The compounds of formula I can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The amount of compound of formula I or VII provided to a patient will vary depending upon what is being administered, the purpose of the administration, such as prophylaxis or therapy, the state of the patient, the manner of administration, and the like. In therapeutic applications, compounds of formula I are provided to a patient suffering from a condition in an amount sufficient to treat or at least partially treat the symptoms of the condition and its complications. An amount adequate to accomplish this is a "therapeutically effective amount" as described previously herein. The dosage to be used in the treatment of a specific case must be subjectively determined by the attending physician. The variables involved include the specific condition and the size, age, and response pattern of the patient. The treatment of substance abuse follows the same method of subjective drug administration under the guidance of the attending physician. Generally, a starting dose is about 5 mg per day with gradual increase in the daily dose to about 150 mg per day, to provide the desired dosage level in the patient.

In certain embodiments, the present invention is directed to prodrugs of compounds of formula I. The term "prodrug," as used herein, means a compound that is convertible in vivo by metabolic means (e.g. by hydrolysis) to a compound of formula I. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Delivery Reviews, 8:1-38(1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is hereby incorporated by reference in its entirety.

EXAMPLES

As depicted in the Examples below, in certain exemplary embodiments, compounds are prepared according to the following general procedures. It will be appreciated that although the general methods depict the synthesis of certain compounds of the present invention, the following general methods, in addition to the Schemes set forth above and other methods known to one of ordinary skill in the art, can be applied to all compounds and subclasses and species of each of these compounds, as described herein.

Intermediate 1

(7-bromo-5-chloro-1-benzofuran-2-yl)methanol: To a solution of 3-bromo-5-chloro-2-hydroxybenzaldehyde (47.09 g, 0.20 mol) in (1:1) tetrahydrofuran:ethanol (1000 mL) was added diethyl bromomalonate (57.38 g, 0.24 mol) and potassium tert-butoxide (26.93 g, 0.24 mol) and the reaction mixture was heated at 70° C. for 12 h. The reaction mixture was allowed to cool to room temperature and the solvent was removed in vacuo to provide a crude solid. The solid was dissolved in tetrahydrofuran (1000 mL) and aqueous sodium hydroxide (1.0 M, 250 mL) was added and the reaction mixture was allowed to stir at room temperature for 4 h. The reaction mixture was acidified (pH 1-2) with concentrated aqueous hydrogen chloride and the aqueous layer was extracted with ethyl acetate (3×250 mL), the combined organic layers washed with water (2×250 mL), saturated aqueous sodium chloride (250 mL), dried (magnesium sulfate), and the solvent removed in vacuo to provide the carboxylic acid as a crude solid. To a solution of the carboxylic acid (2.75 g, 0.01 mol) in tetrahydrofuran (100 mL) cooled to 0° C. was added borane-tetrahydrofuran complex (1.0 M, 30 mL) and the reaction mixture was allowed to stir at room temperature for 12 h. The reaction mixture was quenched by the slow addition of methanol. The solvent was removed in vacuo and the residue was purified by flash column chromatography (silica, ethyl acetate:hexanes 3:7) to provide (7-bromo-5-chloro-1-benzofuran-2-yl)methanol 1.59 g (61%) as a white solid. mp 123-126° C.; Anal. calcd for $C_9HgBrClO_2$: C, 41.34; H, 2.31. Found: C, 41.68; H, 2.04.

Intermediate 2

2-[(7-bromo-5-chloro-1-benzofuran-2-yl)methyl]-1H-isoindole-1,3(2H)-dione: To a solution of triphenylphoshine (1.44 g, 5.48 mmol) in toluene (50 mL) cooled to 0° C. was added the diisopropylazadicarboxylate (1.11 g, 5.48 mmol) followed by the phthalimide (0.81 g, 5.48 mmol) and the reaction mixture allowed to stir for 10 min. The (7-bromo-5-chloro-1-benzofuran-2-yl)methanol (1.37 g, 5.22 mmol) was then added and the reaction was allowed to stir at 0° C. an additional 1 h. The reaction mixture was then quenched with water (1 mL) and the solvent was removed in vacuo to provide a crude solid. The solid was suspended in water (100 mL) and the aqueous layer was extracted with ethyl acetate (3×100 mL), the combined organic extracts were washed with saturated aqueous sodium chloride (50 mL), dried (magnesium sulfate), and the solvent removed in vacuo to provide a crude residue. Purification by flash column chromatography (silica, ethyl acetate:hexanes 1:5) provided 1.73 g (85%) of 2-[(7-bromo-5-chloro-1-benzofuran-2-yl)methyl]-1H-isoindole-1,3(2H)-dione as a white solid. mp 194-198° C.; HRMS-ESI (m/z). $[M+H]^+$ calcd for $C_{17}H_9BrClNO_3$, 388.94545; found, 389.9553.

Intermediate 3

2-[(5-chloro-7-phenyl-1-benzofuran-2-yl)methyl]-1H-isoindole-1,3(2H)-dione: To a suspension of the 2-[(7-bromo-5-chloro-1-benzofuran-2-yl)methyl]-1H-isoindole-1,3(2H)-dione (0.500 g, 1.28 mmol), dichlorobis(tro-o-tolylphosphine)palladium(II) (0.101 g, 0.128 mmol), and potassium carbonate (0.531 g, 3.84 mmol) in dioxane (20 mL) and water (1 mL) heated to 90° C. was added phenylboronic acid (0.390 g, 3.20 mmol) and the reaction allowed to stir for 1 h. The reaction was cooled to room temperature, filtered (celite), and the solvent removed in vacuo to provide a crude residue. Purification by flash column chromatography (silica, ethyl acetate:hexanes 1:4) gave 0.422 g (85%) of 2-[(5-chloro-7-phenyl-1-benzofuran-2-yl)methyl]-1H-isoindole-1,3(2H)-dione as a white solid. mp 163-166° C.

The following compounds were prepared generally according to the procedure described for Intermediate 3:

Intermediate 4

2-{[5-chloro-7-(2-fluorophenyl)-1-benzofuran-2-yl]methyl}-1H-isoindole-1,3(2H)-dione: From 2-[(7-bromo-5-chloro-1-benzofuran-2-yl)methyl]-1H-isoindole-1,3(2}1)-dione and 2-fluorophenylboronic acid gave 2-{[5-chloro-7-(2-fluorophenyl)-1-benzofuran-2-yl]methyl }-1H-isoindole-1,3(2H)-dione (63%) as a white solid. mp 138-143° C.

Intermediate 5

2-{[5-chloro-7-(2-chlorophenyl)-1-benzofuran-2-yl]methyl}-1H-isoindole-1,3(2H)-dione: From 2[(7-bromo-5-chloro-1-benzofuran-2-yl)methyl]-1H-isoindole-1,3(2H)-dione and 2-chlorophenylboronic acid gave 2-{[5-chloro-7-(2-chlorophenyl)-1-benzofuran-2-yl]methyl}-1H-isoindole-1,3(2H)-dione (69%) as a white solid. mp 153-158° C.

Intermediate 6

2-{[5-chloro-7-(2-methylphenyl)-1-benzofuran-2-yl]methyl)-1H-isoindole-1,3(2H)-dione: From 2-[(7-bromo-5-chloro-1-benzofuran-2-yl)methyl]-1H-isoindole-1,3(2H)-dione and 2-methylphenylboronicacid gave 2-{[5-chloro-7-(2-methylphenyl)-1-benzofuran-2-yl]methyl}-1H-isoindole-1,3(2H)- dione (62%) as a white solid. mp 163-167° C.

Intermediate 7

2-{[5-chloro-7-(2-methoxyphenyl)-1-benzofuran-2-yl]methyl}-1H-isoindole-1,3(2H)-dione: From 2-[(7-bromo-5-chloro-1-benzofuran-2-yl)methyl]-1H-isoindole-1,3(2H)-dione and 2-methoxyphenylboronic acid gave 2-{(5-chloro-7-(2-methoxyphenyl)-1-benzofuran-2-yl]methyl}-1H-isoindole-1,3(2H)- dione (63%) as a white solid. mp 149-153° C.

Intermediate 8

2-((5-chloro-7-[2-(trifluoromethyl)phenyl]-1-benzofuran-2-yl}methyl)-1H-isoindole-1,3(2H)-dione: From 2-[(7-bromo-5-chloro-1-benzo furan-2-yl)methyl]-1H-isoindole-1,3(2H)-dione and 2-(trifluoromethyl)phenylboronic acid gave 2-((5-chloro-7-[2-(trifluoromethyl)phenyl]-1-benzofuran-2-yl}methyl)-1H-isoindole-1,3(2H)-dione (60%) as a white solid. mp 160-163° C.

Example 1

[(5-chloro-7-phenyl-1-benzofuran-2-yl)methyl]amine: To a suspension of 2-[(7-phenyl-5-chloro-1-benzofuran-2-yl)methyl]-1H-isoindole-1,3(2H)-dione (0.382 g, 0.985 minol) in ethanol (10 mL) was added the methylamine (33% in ethanol, 20 mL) and the reaction mixture was heated to 70° C. and allowed to stir for 1 h. The reaction mixture was allowed to cool to room temperature and the solvent removed in vacuo. The residue was dissolved in ethyl acetate (50 mL) and washed with water (2×20 mL), saturated aqueous sodium bicarbonate (20 mL), saturated aqueous sodium chloride (20 mL), dried (magnesium sulfate), and the solvent removed in vacuo. Purification by flash column chromatography (silica, 10% ammonium hydroxide in methanol:ethyl acetate 1:9) provided a colorless oil that was dissolved in isopropanol (2 mL) and hydrogen chloride (1.0 N in diethyl ether, 5 mL) was added. The resulting precipitate was filtered, washed (diethylether), and dried to afford 0.165 g (57%) of [(5-chloro-7-phenyl-1-benzofuran-2-yl)methyl]amine as a white solid. mp>225° C.

The following compounds were prepared generally according to the procedure described for Example 1:

Example 2

{[5-chloro-7-(2-fluorophenyl)-1-benzofuran-2-yl]methyl}amine: From 2-{[5-chloro-7-(2-fluorophenyl)-1-benzofuran-2-yl]methyl}-1H-isoindole-1,3(2H)-dione gave {[5-chloro-7-(2-fluorophenyl)-1-benzofuran-2-yl]methyl}amine (25%) as a white solid. mp 218-223° C. (dec).

Example 3

{[5-chloro-7-(2-chlorophenyl)-1-benzofuran-2-yl]methyl}amine: From 2-{[5-chloro-7-(2-chlorophenyl)-1-benzofuran-2-yl]methyl}-1H-isoindole-1,3(2H)-dione gave {[5-chloro-7-(2-chlorophenyl)-1-benzofuran-2-yl]methyl}amine (32%) as a white solid. mp 247-250° C. (dec).

Example 4

{[5-chloro-7-(2-methylphenyl)-1-benzofuran-2-yl]methyl}amine: From 2-{[5-chloro-7-(2-methylphenyl)-1-benzofuran-2-yl]methyl}-1H-isoindole-1,3(2H)-dione gave {[5-chloro-7-(2-methylphenyl)-1-benzofuran-2-yl]methyl}amine (33%) as a white solid. mp 219-222° C. (dec).

Example 5

{[5-chloro-7-(2-methoxyphenyl)-1-benzofuran-2-yl]methyl}amine: From 2-{[5-chloro-7-(2-methoxyphenyl)-1-benzofuran-2-yl]methyl}-1H-isoindole-1,3(2H)-dione gave {[5-chloro-7-(2-methoxyphenyl)-1-benzofuran-2-yl]methyl}amine (36%) as a white solid. mp 228-231° C. (dec).

Example 6

({5-chloro-7-[2-(trifluoro methyl) phenyl]-1-benzofuran-2-yl}methyl)amine: From 2-({5-chloro-7-[2-(tnfluoromethyl)phenyl]-1-benzofuran-2-yl}methyl)-1H-isoindole-1,3(2H)-dione gave ({5-chloro-7-[2-(trifluoromethyl)phenyl]-1-benzofuran-2-yl}methyl)amine (20%) as a white solid. mp 215-218° C. (dec)

Example 7

{[7-(2,6-dichlorophenyl)-5-fluoro-1-benzofuran-2-yl]methyl) amine: From 2-[7-(2,6-dichloro-phenyl)-5-fluoro-benzofuran-2-ylmethyl]-isoindole-1,3-dione gave {[7-(2,6-dichlorophenyl)-5-fluoro-1-benzofuran-2-yl]methyl}amine as a white solid. mp 213-215° C.

Example 8

{[5-fluoro-7-(2-methylphenyl)-1-benzofuran-2-yl]methyl}amine: From 2-(5-fluoro-7-(2-methylphenyl)-benzofuran-2-ylmethyl)-isoindole-1,3-dione gave {[5-fluoro-7-(2-methylphenyl)-1-benzofuran-2-yl]methyl}amine as a white solid. mp 193-194° C.

Example 9

{[7-(2,4-dichlorophenyl)-5-fluoro-1-benzofuran-2-yl]methyl}amine: From 2-17-(2,4-dichlorophenyl)-5-fluoro-benzofuran-2-ylmethyl]-isoindole-1,3-dione gave {[7-(2,4-dichlorophenyl)-5-fluoro-1-benzofuran-2-yl]methyl}amine as a white solid. mp 190° C. (dec).

Example 10

1-[5-fluoro-7-(2-methoxyphenyl)-1-benzofuran-2-yl]methanamine: From 2-[5-fluoro-7-(2-methoxyphenyl)-benzofuran-2-ylmethyl]-isoindole-1,3-dione gave 1-[5-fluoro-7-(2-methoxyphenyl)-1-benzofuran-2-yl]methanamine as a white solid. mp 128-130° C.

Example 11

1-[7-(2,5-dichlorophenyl)-5-fluoro-1-benzofuran-2-yl]methanamine: From 2-[7-(2,5-dichlorophenyl)-5-fluoro-benzofuran-2-ylmethyl]-isoindole-1,3-dione gave 1-[7-(2,5-dichlorophenyl)-5-fluoro-1-benzofuran-2-yl]methanamine as a white solid. mp 245-247° C.

Example 12

1-[7-(2-methylphenyl)-1-benzofuran-2-yl]methanamine: From 2-(7-(2-methylphenyl)-1-benzofuran-2-ylmethyl)-isoindole-1,3-dione gave 1-[7-(2-methylphenyl)-1-benzofuran-2-yl]methanamine as a white solid. mp 222-224° C.

Example 13

1-[7-(4-chloro-2-methylphenyl)-5-fluoro-1-benzofuran-2-yl]methanamine: From 2-[7-(4-chloro-2-methylphenyl)-5-fluoro-benzofuran-2-ylmethyl]-isoindole-1,3-dione gave 1-[7-(4-chloro-2-methylphenyl)-5-fluoro-1-benzofuran-2-yl]methanamine as a white solid. mp 172-174° C.

Example 14

1-[7-(5-chloro-2-methylphenyl)-5-fluoro-1-benzofuran-2-yl]methanamine: From 2-[7-(5-chloro-2-methylphenyl)-5-fluoro-benzofuran-2-ylmethyl]-isoindole-1,3-dione gave 1-[7-(5-chloro-2-methylphenyl)-5-fluoro-1-benzofuran-2-yl]methanamine as a white solid. mp 208-210° C.

Example 15

1-[7-(2,6-dichlorophenyl)-1-benzofuran-2-yl]methanamine: From 2-[7-(2,6-dichlorophenyl)-benzofuran-2-ylmethyl]-isoindole-1,3-dione gave 1-[7-(2,6-dichlorophenyl)-1-benzofuran-2-yl]methanamine as a white solid. mp 260-262° C.

Example 16

1-[6-chloro-7-(2-chlorophenyl)-1-benzofuran-2-yl]methanamine: From 2-[6-chloro-7-(2-chlorophenyl)-benzofuran-2-ylmethyl]-isoindole-1,3-dione gave [6-chloro-7-(2-chlorophenyl)-1-benzofuran-2-yl]methanamine as a white solid. mp 208-210° C.

Example 17

1-[7-(2-chlorophenyl)-6-fluoro-1-benzofuran-2-yl]methanamine: From 2-[7-(2-chlorophenyl)-6-fluoro-benzofuran-2-ylmethyl]-isoindole-1,3-dione gave 1-[7-(2-chlorophenyl)-6-fluoro-1-benzofuran-2-yl]methanamine as a white solid. mp >250° C.

Biological Assays

The ability of the compounds of this invention to act as 5-HT$_{2C}$ agonists and partial agonists was established using several standard pharmacological test procedures; the procedures used and results obtained are provided below. In the test procedures, 5-HT stands for 5-hydroxytryptamine, mCPP stands for meta-chlorophenylpiperazine, and DOI stands for 1-(2,5-dimethoxy-4-iodophenyl)isopropylamine.

To evaluate the affinity of various compounds of formula I for activity at the 5-HT$_{2C}$ receptor, a CHO (Chinese Hamster Ovary) cell line transfected with the cDNA expressing the human 5-hydroxytryptamine-2C (h5-HT$_{2C}$) receptor was maintained in DMEM (Dulbecco's Modified Eagle Media) supplied with fetal calf serum, glutamine, and the markers: guaninephosphoribosyl transferase (GTP) and hypoxanthinethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10-25 μL volumes. Bovine Serum Albumin (BSA) was used as the standard in the protein determination by the method of Lowry et al., (J. Biol. Chem., 193:265 (1951). The volume of the suspended cell membranes was adjusted with 50 mM Tris.HCl buffer containing: 0.1% ascorbic acid, 10 mM pargyline and 4 mM CaCl$_2$ to give a tissue protein concentration of 1-2 mg per ml of suspension. The preparation membrane suspension (many times concentrated) was aliquoted in 1 ml volumes and stored at −70° C. until used in subsequent binding experiments.

Binding measurements were performed in a 96 well microtiter plate format, in a total volume of 200 μL. To each well was added: 60 μL of incubation buffer made in 50 mM Tris.HCl buffer, pH 7.4 and containing 4 mM CaCl$_2$; 20 μL of [$^{125}$I] DOI (S.A., 2200 Ci/mmol, NEN Life Science).

The dissociation constant, KD of [$^{125}$I] DOI at the human serotonin 5-HT$_{2C}$ receptor was 0.4 nM by saturation binding with increasing concentrations of [$^{125}$I] DOI. The reaction was initiated by the final addition of 100 μL of tissue suspension containing 50 μg of receptor protein. Nonspecific binding is measured in the presence of 1 μM unlabeled DOI added in 20.0 μL volume. Test compounds were added in 20.0 μL. The mixture was incubated at room temperature for 60 min. The incubation was stopped by rapid filtration. The bound ligand-receptor complex was filtered off on a 96 well unifilter with a Packard ®Filtermate 196 Harvester. The bound complex caught on the filter disk was dried in a vacuum oven heated to 60° C. and the radioactivity measured by liquid scintillation with 40 μL Microscint-20 scintillant in a Packard TopCount® equipped with six (6) photomultiplier detectors.

Specific binding is defined as the total radioactivity bound less the amount bound in the presence of 1 μM unlabeled DOI. Binding in the presence of varying concentrations of test drugs is expressed as percent of specific binding in the absence of drug. These results are then plotted as log % bound vs log concentration of test drug. Non linear regression analysis of data points yields both the IC$_{50}$ and the K$_i$ values of test compounds with 95% confidence limits. Alternatively, a linear regression line of decline of data points is plotted, from which the IC$_{50}$ value can be read off the curve and the K$_i$ value determined by solving the following equation:

$$K_i = \frac{IC_{50}}{1 + L/K_D}$$

where L is the concentration of the radioactive ligand used and the K$_D$ is the dissociation constant of the ligand for the receptor, both expressed in nM.

The following K$_i$'s (95% confidence interval) are provided for various reference compounds in Table 2, below:

TABLE 2

K$_i$ Data for Reference Compounds

| Compound | K$_i$ |
|---|---|
| Ritanserin | 2.0 (1.3-3.1) nM |
| Ketanserin | 94.8 (70.7-127.0) nM |
| Mianserin | 2.7 (1.9-3.8) nM |
| Clozapine | 23.2 (16.0-34.0) nM |
| Methiothepin | 4.6 (4.0-6.0) nM |
| Methysergide | 6.3 (4.6-8.6) nM |
| Loxapine | 33.0 (24.0-47.0) nM |
| mCPP | 6.5 (4.8-9.0) nM |
| DOI | 6.2 (4.9-8.0) nM |

The ability of the compounds of formula I to produce an agonist response at brain 5-HT$_{2C}$ was assessed by determining their effect on calcium mobilization using the following procedure: CHO cells stably expressing the human 5-HT$_{2C}$ receptor were cultured in Dulbecco's modified Eagle's medium (DMEM) supplemented with 10% fetal bovine serum and non-essential amino acids. Cells were plated at a density of 40K cells/well in 96-well clear-bottom black-wall plates 24 hours prior to the evaluation of 5-HT$_{2C}$ receptor-stimulated calcium mobilization. For calcium studies, cells were loaded with the calcium indicator dye Fluo-3-AM in Hank's buffered saline (HBS) for 60 minutes at 37° C. Cells were washed with HBS at room temperature and transferred to the fluorometric imaging plate reader (FLIPR, Molecular Devices, Sunnyvale, Calif.) for acquisition of calcium images. Excitation at 488 nm was achieved with an Argon ion laser and a 510-560 nm emission filter was used. Fluorescence images and relative intensities were captured at 1 second intervals and cells were stimulated by addition of agonist after 10 baseline measurements using the internal fluidics module of the FLIPR. An increase in fluorescence counts corresponds to an increase in intracellular calcium.

For the evaluation of agonist pharmacology the calcium changes in response to different concentrations of agonist were determined using a maximum minus minimum calculation of the raw fluorescence count data. Calcium changes were then expressed as a percentage of the response observed with a maximally effective concentration of 5-HT. EC$_{50}$ values were estimated by non-linear regression analysis of the log-concentration % maximum 5-HT response curves using the 4-parameter logistic function. In certain embodiments, compounds of the present invention provide an EC$_{50}$ of ≦about 1000 nM. In other embodiments, compounds of the present invention provide an EC$_{50}$ of ≦about 100 nM, in yet other embodiments ≦about 20 nM, in still other embodiments ≦about 5 nM, and certain embodiments ≦about 2 nM.

The following $EC_{50}$'s are provided for various reference compounds in Table 3, below

TABLE 3

| EC$_{50}$ Data for Reference Compounds: | |
| --- | --- |
| Compound | EC$_{50}$ |
| 5-HT | 0.5 nM |
| DOI | 0.5 nM |
| mCPP | 5.4 nM |

Table 4 below shows the results of the activity of selected compounds of this invention in the assays described above. The compound numbers correspond to the compound numbers in Table 1, supra. Compounds having an activity designated as "A" provided a $K_i$ value between 0.01 to 1 nM; compounds having an activity designated as "B" provided a $K_i$ value between 1 nM and 10 nM; and compounds having an activity designated as "C" provided a $K_i$ value between 10 nM and 100 nM. Compounds having an activity designated as "D" provided an $EC_{50}$ value of less than 10 nM; compounds having an activity designated as "E" provided a an $EC_{50}$ value between 10 nM and 200 nM; and compounds having an activity designated as "F" provided a an $EC_{50}$ value between 200 nM and 2000 nM.

TABLE 4

| 5-HT$_{2C}$ Activity of Selected Compounds | | | |
| --- | --- | --- | --- |
| Compound | 5-HT$_{2C}$ Binding | 5-HT$_{2C}$ Function | |
| Number | K$_i$ avg (nM) | EC$_{50}$ (nM) | EMax (%) |
| 1 | C | F | 70 |
| 2 | B | F | 80 |
| 3 | — | D | 100 |
| 4 | — | E | 90 |
| 5 | B | E | 90 |
| 6 | C | F | 90 |
| 7 | A | D | 100 |
| 8 | B | D | 90 |
| 9 | A | D | 90 |
| 10 | B | E | 80 |
| 11 | A | D | 70 |
| 12 | B | D | 70 |
| 13 | B | E | 80 |
| 14 | B | E | 80 |
| 15 | A | D | 90 |
| 16 | A | D | 90 |

The compounds of this invention thus have affinity for and agonist or partial agonist activity at brain serotonin 5-HT$_{2C}$ receptors. They are therefore of interest for the treatment of the central nervous system conditions described previously herein.

The entire disclosure of each patent, patent application, and publication cited or described in this document is hereby incorporated by reference.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

We claim:
1. A compound of formula I:

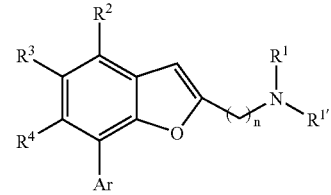

or pharmaceutically acceptable salts thereof, wherein:
each of $R^1$ and $R^{1'}$ is independently hydrogen, methyl, ethyl, 2-fluoroethyl, 2,2-difluoroethyl or cyclopropyl;
each of $R^2$, $R^3$ and $R^4$ is independently hydrogen, halogen, OH, lower alkyl, lower alkoxy, trifluoromethyl, trifluoromethoxy, or CN;
Ar is thienyl, furyl, pyridyl, or phenyl wherein Ar is optionally substituted with one or more $R^x$ groups;
each $R^x$ is independently halogen, —OH, —CN, lower alkyl, lower alkoxy, —CF$_3$, or —OCF$_3$; and
n is one or two.

2. The compound according to claim 1, wherein one of $R^1$ and $R^{1'}$ is hydrogen and the other of $R^1$ and $R^{1'}$ groups of formula I is hydrogen, methyl, ethyl, 2-fluoroethyl, 2,2-difluoroethyl or cyclopropyl.

3. The compound according to claim 2, wherein both of $R^1$ and $R^{1'}$ is hydrogen.

4. The compound according to claim 1, wherein neither $R^1$ nor $R^{1'}$ is hydrogen.

5. The compound according to claim 1, wherein $R^2$, $R^3$ and $R^4$ are all hydrogen.

6. The compound according to claim 1, wherein at least one of $R^2$, $R^3$ and $R^4$ is independently halogen.

7. The compound according to claim 1, wherein $R^2$ is hydrogen and $R^3$ and $R^4$ are independently halogen, OH, lower alkyl, lower alkoxy, trifluoromethyl, trifluoromethoxy, or CN.

8. The compound according to claim 7, wherein $R^2$ and $R^4$ are both hydrogen and $R^3$ is halogen, OH, lower alkyl, lower alkoxy, trifluoromethyl, or trifluoromethoxy.

9. The compound according to claim 7, wherein $R^2$ and $R^3$ are both hydrogen and $R^4$ is halogen, OH, lower alkyl, lower alkoxy, trifluoromethyl, or trifluoromethoxy.

10. The compound according to claim 1, wherein Ar is unsubstituted phenyl.

11. The compound according to claim 1, wherein Ar is phenyl with at least one substituent in the ortho position.

12. The compound according to claim 11, wherein Ar is phenyl with at least one substituent in the ortho position selected from halogen, lower alkyl, lower alkoxy, or trifluoromethyl.

13. The compound according to claim 1, wherein Ar is selected from:

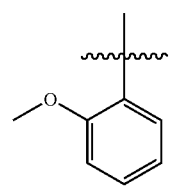

i

-continued
ii 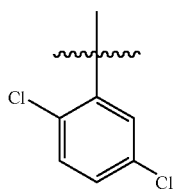
iii 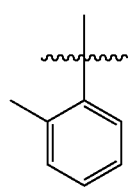
iv 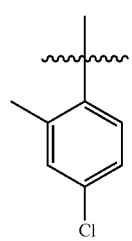
v 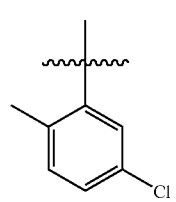
vi 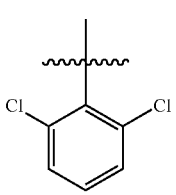
vii 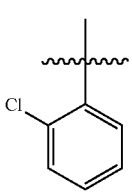
viii 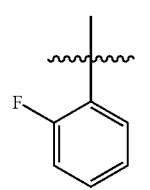
ix
-continued
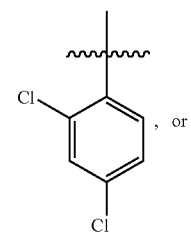, or
x
xi
14. The compound according to claim 1, wherein said compound is of formula II, III, IV, V, VI, or VII:
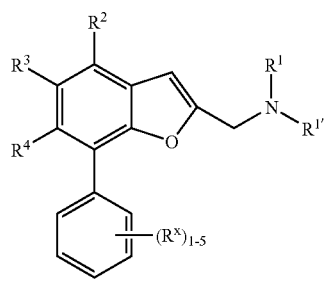
II
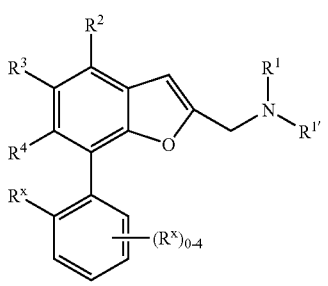
III
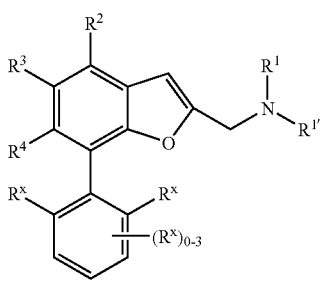
IV

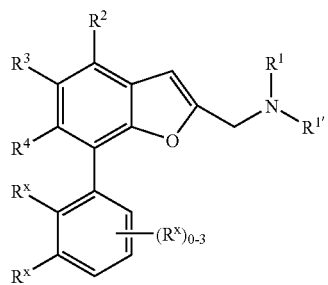
V
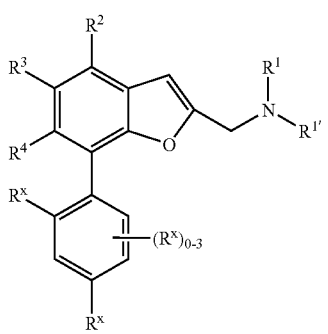
VI
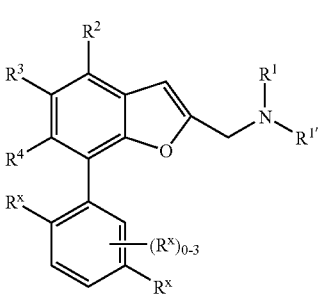
VII
or a pharmaceutically acceptable salt thereof, wherein each $R^x$ is independently halogen, OH, lower alkyl, lower alkoxy, trifluoromethyl, trifluoromethoxy, or CN.
15. The compound according to claim 1, wherein said compound is selected from:
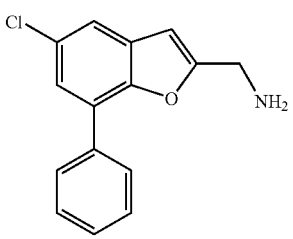
I-1
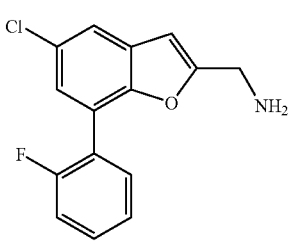
I-2
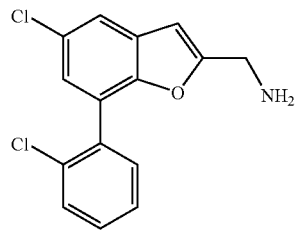
I-3
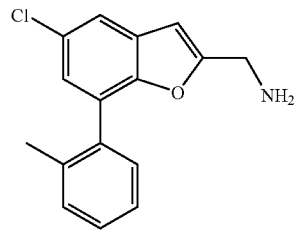
I-4
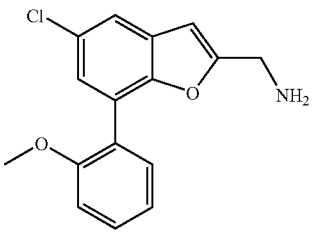
I-5
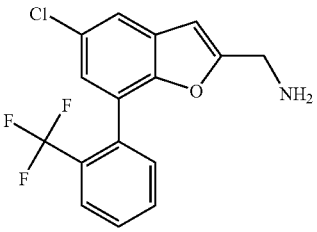
I-6
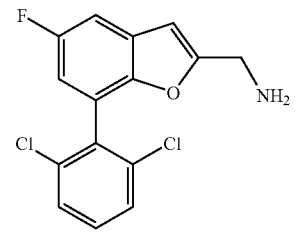
I-7
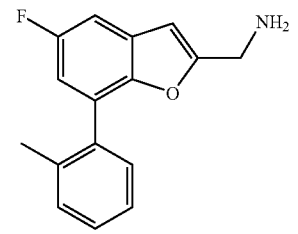
I-8

-continued
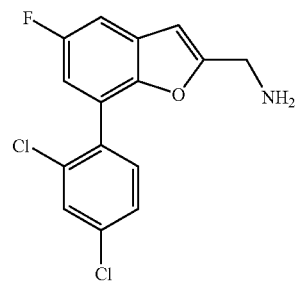
I-9
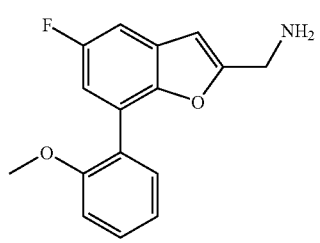
I-10
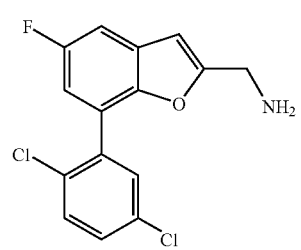
I-11
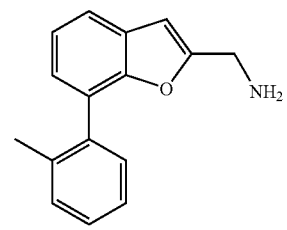
I-12
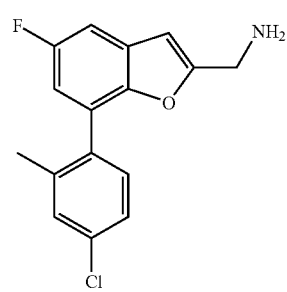
I-13
-continued
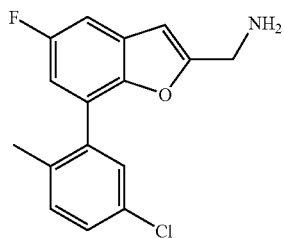
I-14
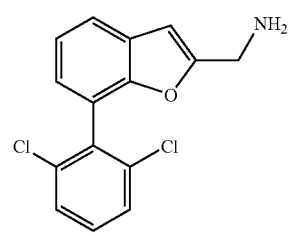
I-15
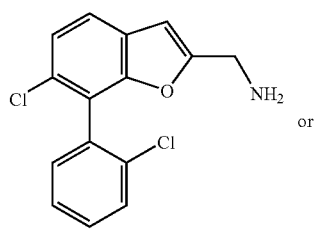
I-16
or
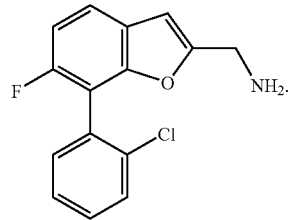
I-17
16. A composition comprising a compound according to claim 1, and one or more pharmaceutically acceptable carriers.
* * * * *